US012672620B2

(12) United States Patent
Lowe

(10) Patent No.: US 12,672,620 B2
(45) Date of Patent: Jul. 7, 2026

(54) PLANT PROPAGATION SYSTEMS, DEVICES AND METHODS

(71) Applicant: Lowes TC Pty Ltd, Tumbi Umbi (AU)

(72) Inventor: Greg Lowe, Tumbi Umbi (AU)

(73) Assignee: Lowes TC Pty Ltd, Tumbi Umbi (AU)

( * ) Notice: Subject to any disclaimer, the term of this patent is extended or adjusted under 35 U.S.C. 154(b) by 148 days.

(21) Appl. No.: 17/259,596

(22) PCT Filed: Jul. 12, 2019

(86) PCT No.: PCT/AU2019/050740
§ 371 (c)(1),
(2) Date: Jan. 12, 2021

(87) PCT Pub. No.: WO2020/010412
PCT Pub. Date: Jan. 16, 2020

(65) Prior Publication Data
US 2021/0315164 A1 Oct. 14, 2021

(30) Foreign Application Priority Data

Jul. 13, 2018 (AU) ................................. 2018902543
Jul. 13, 2018 (AU) ................................. 2018902545
Jul. 13, 2018 (AU) ................................. 2018902546

(51) Int. Cl.
*A01H 4/00* (2006.01)
*A01G 2/10* (2018.01)
(Continued)

(52) U.S. Cl.
CPC ............... *A01H 4/001* (2013.01); *A01G 2/10* (2018.02); *A01G 9/0293* (2018.02);
(Continued)

(58) Field of Classification Search
CPC ........ A01G 2/10; A01G 9/0299; A01G 9/029; A01G 9/0293; A01G 9/0295; A01H 4/003
See application file for complete search history.

(56) References Cited

U.S. PATENT DOCUMENTS 5,548,924 A * 8/1996 Mekler .................. A01H 4/001
47/60
7,207,138 B1 4/2007 Hauser
(Continued)

FOREIGN PATENT DOCUMENTS

| CN | 1041258 A | 4/1990 |
| CN | 1512904 A | 7/2004 |
| | (Continued) | |

OTHER PUBLICATIONS

Extended European Search Report issued to Application No. EP 19834273.5, dated Mar. 23, 2022.
(Continued)

*Primary Examiner* — Kristen C Hayes
(74) *Attorney, Agent, or Firm* — MARSHALL, GERSTEIN & BORUN LLP; Michael P. Furmanek

(57) ABSTRACT
A plant propagation system is provided that includes a holder for holding at least two plants in relative spaced apart relation to enable a predetermined operation (such as, for example, a cutting operation) to be performed on each of the plants within the holder during a single pass.

14 Claims, 11 Drawing Sheets

(51) Int. Cl.
    *A01G 9/029*     (2018.01)
    *A01G 27/00*     (2006.01)
(52) U.S. Cl.
    CPC ......... *A01G 9/0299* (2018.02); *A01G 27/005*
        (2013.01); *A01H 4/002* (2021.01); *A01H*
        *4/003* (2013.01)

(56) References Cited

U.S. PATENT DOCUMENTS

| | | | |
|---|---|---|---|
| 2010/0132065 A1 | 5/2010 | Forsberg | |
| 2013/0180171 A1* | 7/2013 | Oldenburg ........... | A01G 9/0295 |
| | | | 47/63 |
| 2017/0318753 A1 | 11/2017 | Teasdale | |
| 2018/0014485 A1 | 1/2018 | Whitcher et al. | |

FOREIGN PATENT DOCUMENTS

| | | | |
|---|---|---|---|
| CN | 202211050 U | 5/2012 | |
| CN | 102577919 A | 7/2012 | |
| CN | 102665392 A | 9/2012 | |
| CN | 106105888 A | 11/2016 | |
| CN | 206302788 U | 7/2017 | |
| EP | 0631467 A1 | 1/1995 | |
| EP | 0858735 A1 | 8/1998 | |
| JP | S49-079869 A | 8/1974 | |
| JP | H02-190118 A | 7/1990 | |
| JP | H03-107438 A | 5/1991 | |
| JP | H04-126069 A | 4/1992 | |
| JP | 2001-204283 A | 7/2001 | |
| JP | 2001-352837 A | 12/2001 | |
| JP | 2003-102300 A | 4/2003 | |
| JP | 2014-030377 A | 2/2014 | |
| WO | WO-1991015110 A1 | 10/1991 | |
| WO | WO-199203913 A1 | 3/1992 | |
| WO | WO-0164844 A1 * | 9/2001 | ............ A01H 4/001 |
| WO | WO-2001064844 A1 | 9/2001 | |
| WO | WO-2011014933 A1 | 2/2011 | |
| WO | WO-2012/096568 A1 | 7/2012 | |
| WO | WO-2015053542 A1 | 4/2015 | |
| WO | WO-2015164608 A1 | 10/2015 | |
| WO | WO-2016/129683 A1 | 8/2016 | |
| WO | WO-2016196714 A1 * | 12/2016 | .............. A01H 4/00 |
| WO | WO-2018024369 A1 | 2/2018 | |
| WO | WO-2018/041308 A1 | 3/2018 | |
| WO | WO-2020010412 A1 | 1/2020 | |

OTHER PUBLICATIONS

Third Party Observation issued to Application No. PCT/AU2019/050740, date of submission Nov. 20, 2020.
International Search Report for International Application No. PCT/AU2019/050740, dated Sep. 25, 2019.
International Preliminary Report on Patentability for International Application No. PCT/AU2019/050740, dated Jul. 8, 2020.
Office Action, Japanese patent application No. 2021-502764, dated Mar. 22, 2023.
Office Action, Chinese patent application No. 201980059907.6, mailing date Aug. 15, 2023.
Office Action, Chinese patent application No. 201980059907.6, mailing date Apr. 30, 2024.
Office Action, Japanese patent application No. 2021-502764, mailing date Oct. 24, 2023.
Office Action, Japanese patent application No. 2024-113174, mailing date Sep. 30, 2025.

\* cited by examiner

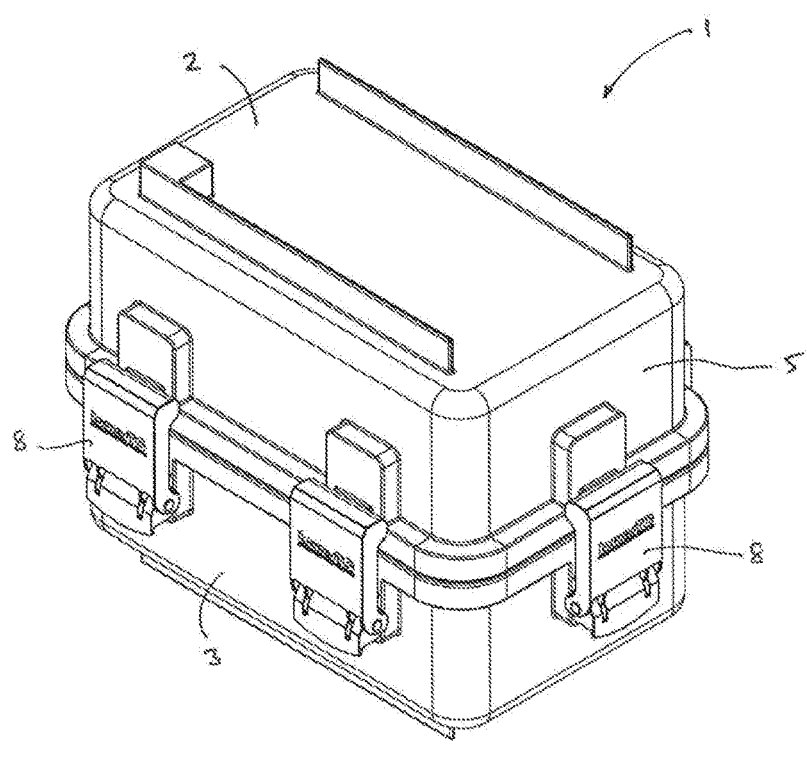
FIGURE 1A
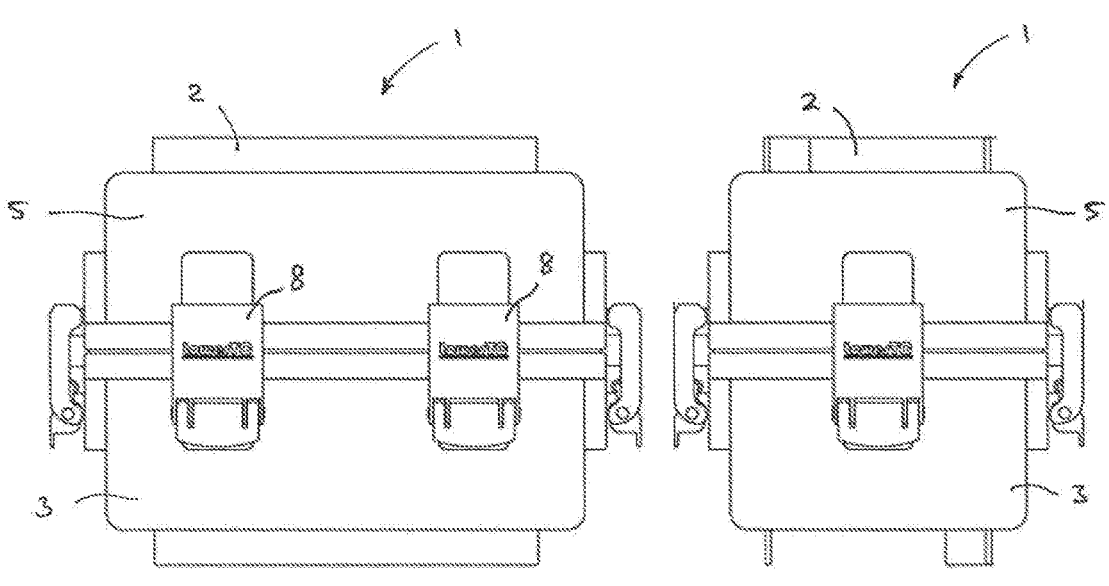
FIGURE 1B                    FIGURE 1C

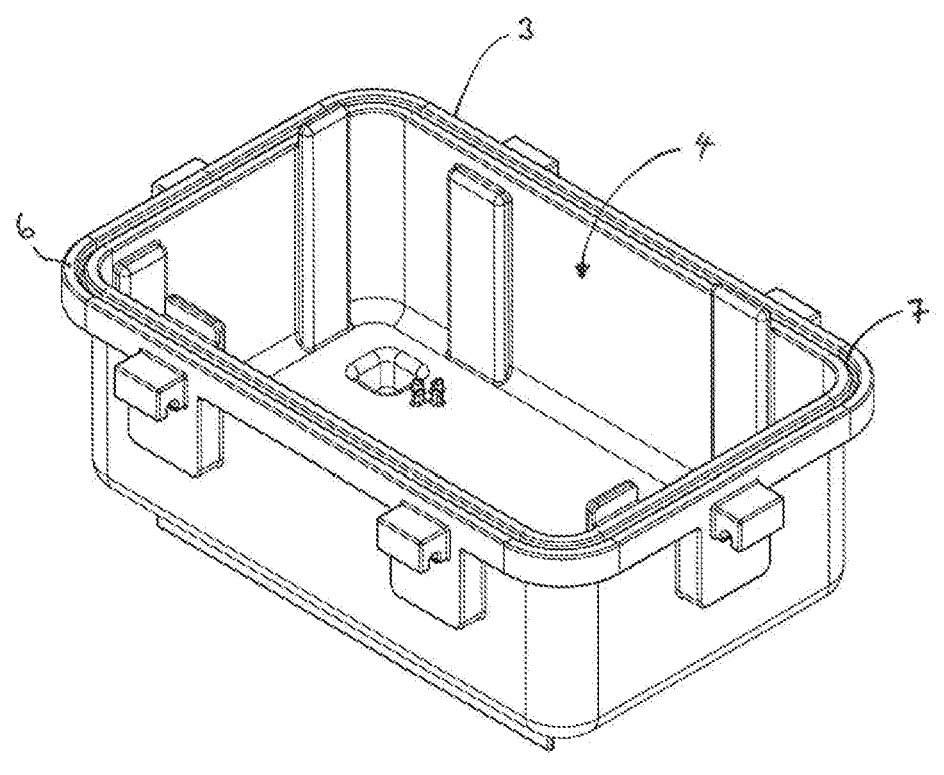
FIGURE 2A
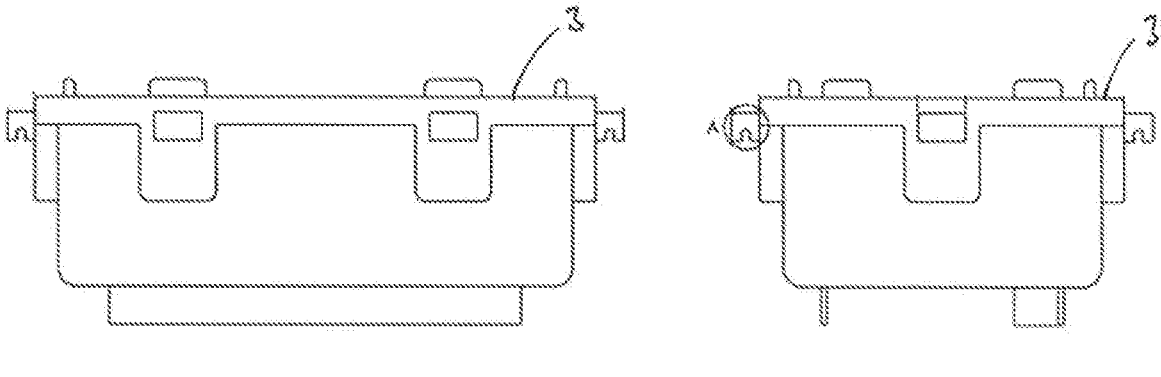
FIGURE 2B                                    FIGURE 2C

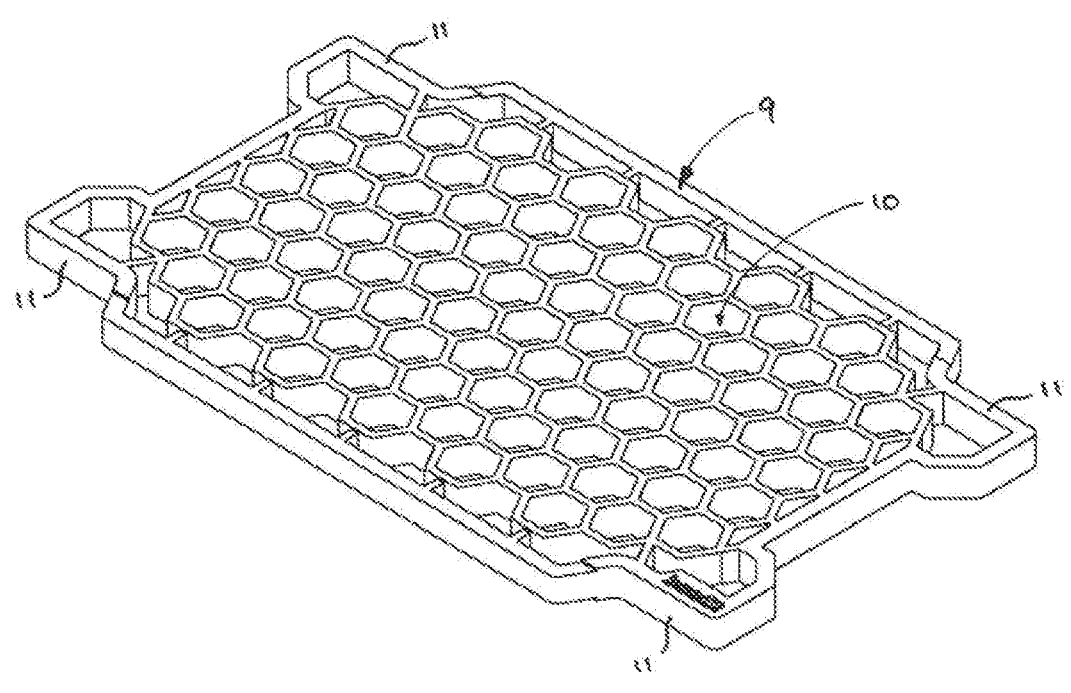
FIGURE 3A
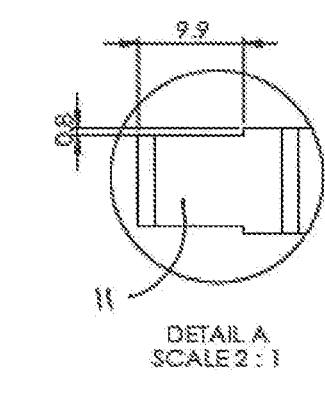
DETAIL A
SCALE 2 : 1
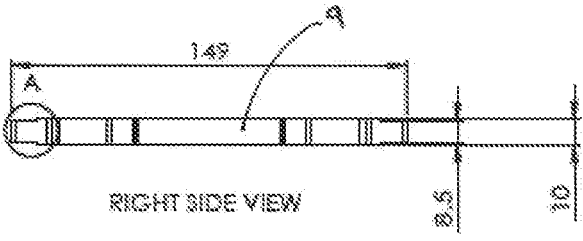
RIGHT SIDE VIEW
FIGURE 3B

MEDIA IN BAG
BIO REACTOR
EMPTY

MEDIA
POCKET

MEDIA
BAG
FULL

INFLATABLE
BAG
DEFLATED

MEDIA GRAVITY
FEEDING INTO
BAG

MEDIA
POCKET

MEDIA
BAG
FILLING

INFLATABLE
BAG
DEFLATED

MEDIA IN
BIO REACTOR
FULL

MEDIA
POCKET

MEDIA
BAG
EMPTY

INFLATABLE
BAG
INFLATED
USING
COMPRESSED AIR

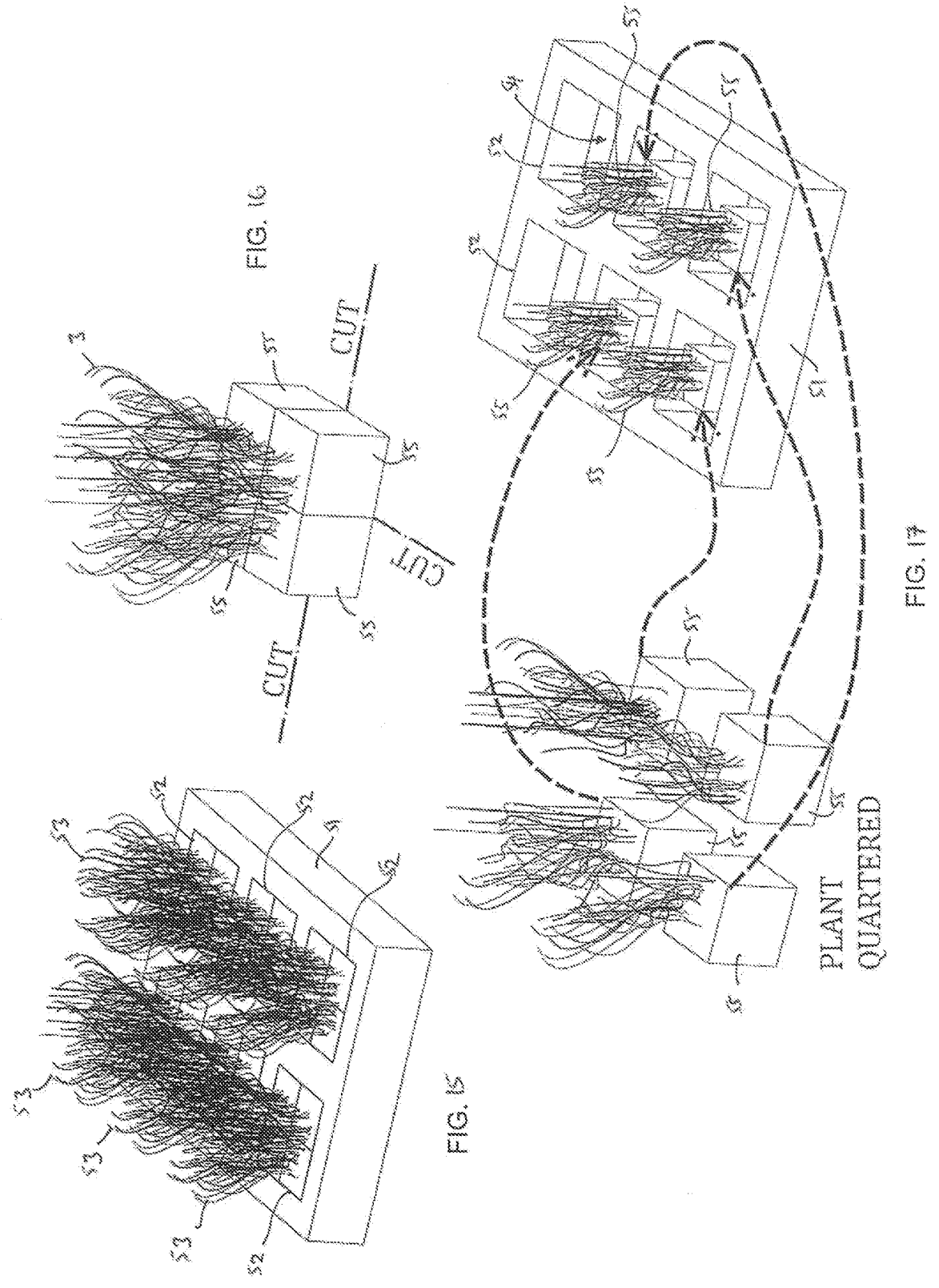

PLANT PROPAGATION SYSTEMS, DEVICES AND METHODS

CROSS-REFERENCE TO RELATED APPLICATIONS

This is the United States national phase of International Patent Application No. PCT/AU2019/050740, filed Jul. 12, 2019, which claims the priority benefit of Australian Provisional Application No.'s 2018902543, 2018902545, and 2018902546, each filed on 13 Jul. 2018, and whereby the entirety of each provisional application is herein expressly incorporated by reference.

TECHNICAL FIELD

The present disclosure relates to systems, methods and devices for growing and propagating plants, and, more specifically, for use in growing plants under plant tissue culture.

The invention has been developed primarily for use in growing plants under plant tissue culture and will be described predominantly in this context. However, it will be appreciated that the invention is not limited to this particular field of use, being potentially applicable in a wide variety of applications including sterile and non-sterile applications, particularly applications based on greenhouse and outdoor environments.

BACKGROUND

The following discussion of the prior art is intended to place the invention in an appropriate technical context and enable its advantages to be more fully appreciated. However, any references to prior art throughout this specification should not be construed as an express or implied admission that such art is widely known or is common general knowledge in the relevant field.

Commercial Plant Tissue Culture (PTC) is the clonal micro propagation of plants for the horticultural industry including ornamentals for home and landscape, cut flowers, revegetation, horticultural food crops, pharmaceutical crops and forestry. Historically PTC has been an expensive way to propagate plants compared to seed and unrooted cutting production (URC) methods but PTC has found a niche to produce difficult to propagate plants and for plants that must be supplied in a high health status.

It is estimated that approximately 15-20 million PTC are planted in Australia and approximately 500 million PTC are planted worldwide annually but this is only a fraction of the total annual horticultural plant production via seed or unrooted cutting (URC) or standard cutting propagation. For example, individual plant breeder and propagator companies are able to produce over 500 million URC each year of chrysanthemum for cut flower production in Europe; over 800 million sugar cane setts are planted each year in Australia; approximately 1.5 billion forestry trees are produced and shipped by forest tree nurseries annually in the USA.

Many plants would be preferentially produced by PTC except for the cost compared to URC, cuttings or seed as there are advantages to crops coming from PTC compared to seed, cuttings or URC for the grower including high health, non-seasonality, increased branching and overall early growth vigour.

For example, in Australia it is estimated that approximately 160,000 tonnes of high health certified seed potatoes are planted each year by growers. These seed potatoes are produced from 1-2 million high health PTC and then grown and multiplied for up to 4 years in open field sites to reduce the cost to growers. However, doing so exposes the seed potatoes to pathogens for 4 years while being bulked up. By reducing the cost of PTC, the number of PTC used will be increased and number of field production generations reduced or removed allowing farmers to receive higher health stock.

The main cost in PTC is associated with labour, and in some regions, over 80% of the total running costs per PTC produced are production wages. This has led to the movement of PTC companies to lower wage environments.

Further, it is estimated that wages can be significantly reduced (e.g. to 1-3 cents per PTC) in developing countries with wages less than $2 per hour.

However, these countries are experiencing wage growth and are usually far removed from the markets that require the plants, so transport and quarantine is an additional major cost, adding 5-20 cents per PTC for consignments being sent to Australia and similar costs are estimated for other major markets from these countries.

Shipping delays can be catastrophic to the viability of the PTC [and URC] being shipped, and can increase costs by 30% over a year. This results in unreliable supply becoming a major factor for customers. International movement of plants is also a major biosecurity risk for all countries and industries and numerous cases of new diseases being introduced to countries by international trade have been documented.

Plants propagated by PTC sourced from lesser developed countries are still more expensive than seed or cutting production done near the market in more developed countries. Currently in Australia PTC from low wage countries are being sold at $0.25-0.45 per PTC compared to $0.80 to $1+ for Australian grown PTC. This compares to seed, which is available for an average cost of less than $0.05 per seed and URC, which is available for an average cost of $0.10 to $0.40, depending on variety and source. All these products must be grown on to a useable form (i.e. hardened plug) for the end customer/grower and the hardened plug prices are currently around $0.15 to $0.40 for seedlings and $0.30 to $0.75 for cuttings, compared to $0.70 to $1+ for PTC.

It has long been the goal of PTC producers to develop an automated procedure for clonal PTC to enable production to occur close to the market and to allow PTC to be used as a viable alternative to cutting production or seed. If competitive PTC production prices can be achieved, it would also allow PTC production to move back to high wage countries where most clonally produced plants are used. This movement back to high wage countries would in turn remove international shipping and quarantine issues.

In the 1990s Forbio Pty Ltd succeeded in building 4 PTC robots using vision systems and a robot arm with a set of tools that duplicated the work of human operators. However in practice the robots only reduced labour cost by about half at most; plants were still processed individually and high levels of operator involvement was still required. The machine was also prohibitively expensive and unreliable. These machines were in operation with Monsanto Forestry in Indonesia for about 2 years before being shelved.

NuPlant in Queensland, AU has produced the Smartclone robot, a robot arm and tools with a plastic pods system. However, this system still relies on a human worker deciding where to cut/divide the plant, and manually cutting the plants. Thus again, this machine is limited to the speed of a human worker and does not reduce wage costs significantly compared to low wage country costs.

VitroPlus in the Netherlands has automated fern culture by a system which utilises fern gametophytes in a liquid media system which can be blended to allow the mass clonal propagation and dispensing of thousands of plantlets[sporophytes] per hour via a sterile liquid dispensing process. However, ferns have a very different life cycle compared to other plants that allows them to be grown in this manner. This technology has not been successfully used for any other plants except algae.

Nonetheless, VitroPlus is now considered by some as the most successful PTC company and exports to most countries around the world from its base in the Netherlands.

As well as robots, other methods have been tested on a wide range of crops to reduce the cost of plant propagation. Bioreactors are commonly used and many of the methods involve somatic embryogenesis combined with the use of an artificial seed technology to deliver the plant to the consumer. Few (if any) of these have been successfully commercialised as a clonal propagation tool as somatic embryogenesis usually results in unreliable clonal production with many off types/mutations being developed as the somatic embryos are generated.

Furthermore, often physiological changes occur to plants grown in bioreactors that make it more difficult and expensive to grow the plant after the process. Thus, there is a need to provide a system of PTC propagation which addresses one or more of the drawbacks of somatic embryogenesis such as mutation, vitrification and poor regeneration success rates that is common in other existing technologies.

With current technologies, it is estimated that currently one human operator can propagate approximately 150-200 plants per hour. Thus it is an object of the present disclosure to provide a system that can increase the rate of PTC propagation.

Another drawback of the conventional commercial use of PTC is encountered in the "deflasking" stage. During deflasking, seedlings and clones of plants of interest that have been produced and raised in the environmental safety and luxury of a sterile PTC container are removed from the container and 'introduced' to standard plant nursery conditions. Currently, during the deflasking stage, staff in high wage countries individually place the PTC received from low wage countries into plug trays one at a time. This is another major cost for the grower.

PTC is traditionally grown in containers holding from 1 to approximately 50 plants in a random placing across the area of the container. These plants are individually handled at each stage of PTC. These plants are then manually and usually individually moved to the greenhouse for hardening. Contamination is a major issue and as is costs associated with traditional PTC and other greenhouse propagation methods due to human handling.

PTC is traditionally done in sealed containers with a sterile gel media that is sterilised and set into the container before use. The container is usually made of glass or polycarbonate with a polypropylene screw lid and recycled or in a disposable polypropylene container and clip on lid.

The disadvantages of this design are that you cannot change the media or treat the plants without moving to another container with an associated high labour and time cost.

Gelling agents can affect the growth of plants, but most plants which are constantly submerged in liquid media (even partially) often develop physiological conditions such as vitrification (hyperhydricity) that reduces the ability to grow or deflask the plants successfully. Temporary Immersion Systems have successfully overcome the downsides of gelling agents and constant liquid exposure by introducing the liquid media into the plant chamber for a few minutes several times a day to allow the plants to get nutrients and exposure to phytohormones and then be drained and be exposed to lower humidity and air drying so that they don't develop any physiological issues.

Most TIS systems use air pressure and a complex two chamber container or a container with many internal parts to force the liquid media from the bottom up into the plant chamber, thus requiring air pumps and controls as well as air filters and strong seals to maintain a sterile system.

It is an object of the present disclosure to overcome or ameliorate one or more disadvantages of current systems and approaches, or at least to provide a useful alternative.

SUMMARY

According to a first aspect of the invention, there is provided a plant propagation system, including:

a holder for holding at least two plants in relative spaced apart relation, thereby to enable a predetermined operation to be performed on each plant within the holder during a single pass.

In some embodiments, the operation is a cutting operation. In some embodiments, the cutting operation is performed sequentially on individual plants, one at a time. In some embodiments, the cutting operation is performed on two or more of the plants within the holder substantially simultaneously. In some embodiments, the cutting operation is performed on a predetermined number of the plants within the holder substantially simultaneously. In some embodiments, the cutting operation is performed on each plant within the holder substantially simultaneously.

In some embodiments, a cutting mechanism is provided for cutting each plant within the holder. In some embodiments, the cutting mechanism has a cutting element which is movable relative to the holder, thereby to effect the cutting operation. Preferably, the cutting mechanism is configured, or arranged in use, to cut each plant from a direction generally transverse or orthogonal to the longitudinal axis of a stem of each plant. That is, the cutting mechanism preferably is configured to axially or laterally cut each plant, more preferably to axially or laterally cut the stem of each plant.

In some embodiments, the holder includes a tray or plate with two or more openings, each opening being configured to receive at least a portion of a plant. Preferably, each opening is dedicated to receiving a portion of a single plant. Preferably, each opening defines a through bore or passage for the respective plant, whereby the plants can grow upwardly through the tray.

In some embodiments, each tray has the same peripheral profile or shape. In some embodiments, each tray is generally rectangular in shape. In other embodiments, each tray may be generally square, circular, oval, polygonal or other suitable profile including irregular shapes.

Each plate preferably has a predetermined thickness. For example, each plate may have a thickness or height of 8 mm, 10 mm, 12 mm, 15 mm, 18 mm, 20 mm or 25 mm. It will be appreciated that the thickness or height of each plate is not limited to the exemplary values listed above, rather the thickness or height may be selected to suit a particular variety of plant.

In some embodiments, the openings in each tray are all the same shape. Each opening may have a regular or irregular shape. In some embodiments, the openings in each tray are all the same size. In some embodiments, each tray may include openings of various shapes and sizes. In some embodiments, the openings in each tray have a (cross-sectional) shape selected from the group including but not limited to circular, oval, square, rectangular, triangular, hexagonal, and other polygonal shapes.

In some embodiments, the openings in each tray are arranged in a regular or irregular array or pattern. In some embodiments, the openings in each tray are arranged in a polar array. For example, the openings may be arranged to form a square array, an offset array wherein alternate rows are staggered by a predetermined extent (e.g. 50% of the opening size), thereby to enable a reduced spacing between adjacent openings and thus the provision of additional openings per plate, if desired. Preferably, each tray has the same profile and pattern of openings.

In some embodiments, the holder includes two or more trays or plates, the plates being stackable to form a tower of plates. Preferably, each plate has the same shape and configuration. It will be appreciated that the ability to arrange two or more trays or plates in a vertical tower or stack advantageously allows a through passage of a predetermined height appropriate for a particular plant type to be constructed by aligning a hole from one tray with a respective hole of a second tray, and any further trays, stacked on the first tray, wherein the plant can grow upwardly therethrough. In this way, a plurality of trays can be stacked on top of each other such that the respective holes are aligned and the associated through passage or passages are formed with a predetermined height corresponding to the thickness of the trays in the stack of trays.

In some embodiments, each tray is configured so as to be close fittingly received within the base portion of the bioreactor. In some embodiments, each tray is configured such that its width substantially corresponds to an internal width of the base portion of the bioreactor. In some embodiments, each tray is configured such that its length substantially corresponds to an internal length of the base portion of the bioreactor. In some embodiments, each tray is configured such that two or more distinct stacks of trays can be arranged within the base portion of the bioreactor, thereby enhancing the flexibility of the growing process and the manner in which the trays can be manipulated and handled in use. For example, the base portion of the bioreactor and the trays may be configured to receive two, three or four distinct stacks of trays therein.

In certain forms, each tray is sized and configured such that it can be transferred from the bioreactor to the next stage of the growing process, either manually or with the use of existing tray handling equipment (e.g. from a sterile environment to a non-sterile environment). This is particularly advantageous as it avoids the need to transfer the plants from the bioreactor tray to a second stage tray such as, for example, a greenhouse or outdoor tray. In some embodiments, each tray may have one or more connectors for releasably connecting trays together in side-by-side and/or end-to-end relation, thereby to effectively form a larger combined tray. In some embodiments, a first side and/or end of a tray may have one or more first connectors and a second side and/or end of a tray may have one or more second connectors, wherein the respective first and second side and end connectors are adapted to releasably engage with each other to connect two or more trays together. Such a larger combined tray may be advantageously used to facilitate ease of handling of the trays, particularly when the trays contain plants ready to be transferred from a sterile (laboratory)

environment to a non-sterile (greenhouse or outdoor) environment for the next stage of development. It will be appreciated that, in this way, it is possible to produce trays or combined tray arrangements which are sized to work within handling equipment (e.g. manual or automated handling equipment) associated with related downstream processes and systems used in the further development of the plants once they leave the sterile environment.

In some embodiments, each plate or tray has a uniform thickness. In some embodiments, each plate or tray may include one or more portions of reduced thickness, thereby to facilitate selection and removal of a desired tray or sub-set of trays from the stack of trays and/or to facilitate performing an operation between adjacent trays within the stack of trays. In some embodiments, each tray may include a main or central body portion in which the openings are formed, and one or more projections extending outwardly from an edge of the respective tray, thereby to facilitate handling of the trays.

In some embodiments, each tray or plate may have complementary locating elements for locating and releasably retaining adjacent trays in alignment, thereby to facilitate forming of the stack of plates as well as enhancing the structural integrity of the stack. In some embodiments, the complementary locating elements may include a first locating element associated with an upper surface of each tray (e.g. lug or recess) and a second locating element (e.g. recess or lug) associated with a lower surface of each tray, whereby the first locating element can releasably engage the second locating element to locate and align the respective trays. However, it is preferred that no locating elements are formed on the trays such that there is no obstruction extending between adjacent trays, thereby enabling the cutting operation to be performed freely between a pair of adjacent trays.

In some embodiments, the passage defined by the openings of the tray acts to guide and, if necessary, support the plant as it grows up through the passage. Preferably, an inner peripheral surface of a side wall of the respective opening acts to limit the extent of lateral movement of the plant within the passage, thereby to guide the plant in a generally upward or vertical direction. In other embodiments, a dedicated guide member may be provided.

In certain embodiments, the holder may include one or more grasping elements or mechanisms for holding each plant. For example, each grasping element or mechanism may include a jaw or pair of jaws movable between an open position for insertion and removal of the plant and a closed position for holding each plant. In certain embodiments, the grasping element may be biased towards a closed position, for example, by provision of a pretensioned coil spring or other suitable mechanical biasing element.

In some embodiments, the cutting operation may be effected by relative translational sliding movement between a pair of plates. In some embodiments, the cutting mechanism may be configured to perform a cutting operation between a pair of plates in the stack of plates. In some embodiments, the cutting mechanism may be configured to perform a cutting operation between each pair of plates in the stack of plates. In some embodiments, the cutting mechanism may be configured to perform a cutting operation between some of the pairs of plates in the stack. In some embodiments, the cutting mechanism may be configured to perform the cutting operation between each selected pair of plates in the stack substantially simultaneously.

In some embodiments, the cutting mechanism includes a dedicated hand-held cutting tool for manual cutting of the plants, preferably configured for cutting two or more plants simultaneously. In some embodiments, the cutting mechanism is operatively associated with a controller, thereby to facilitate autonomous or semi-autonomous cutting of the plants. For example, the cutting element may be (directly or indirectly) connected to an actuator, thereby to position and move the cutting element relative to the stack of trays, thereby to produce a desired cutting action. In some embodiments, the cutting mechanism (e.g. blade, laser, wire element, etc) may be connected to a linear actuator or as an end effector on a robotic arm.

In some embodiments, the cutting tool includes a cutting element in the form of a blade. In some embodiments, the cutting tool may include a handle portion, with the cutting element connected thereto. In some embodiments, the cutting tool includes a cutting element in the form of a relatively thin plate-like element adapted to be slidably received between a respective pair of adjacent trays, thereby to effect a lateral cutting operation on the plants. In other forms, the cutting mechanism may include a length of small gauge wire that can be slidably received between a respective pair of adjacent trays, thereby to effect the cutting operation.

In some embodiments, the cutting element is movably connected to the handle portion for movement between an operative position in which the blade extends generally away from the handle portion and an inoperative position in which the cutting element is adjacent the handle portion. For example, the cutting element may be pivotally or hinged connected to the handle portion. In some embodiments, the handle is operatively associated with the cutting element such that movement of the handle causes a corresponding movement of the cutting element. In some embodiments, the handle is operatively associated with the cutting element such that a linear movement of the handle in a first direction causes a corresponding cutting movement of the cutting element. In some embodiments, the handle is operatively associated with the cutting element such that a linear movement of the handle in a second direction causes a corresponding retracting movement of the cutting element, thereby to retract the cutting element once a cutting operation has been completed. In some embodiments, the handle is operatively associated with the cutting element such that a rotational movement of the handle in a first direction causes a corresponding cutting movement of the cutting element. In some embodiments, the handle is operatively associated with the cutting element such that a rotational movement of the handle in a second direction causes a corresponding retracting movement of the cutting element, thereby to retract the cutting element once a cutting operation has been completed.

In some embodiments, the cutting element is configured to oscillate or vibrate during the cutting operation. In some embodiments, the oscillations or vibrations may be in a vertical direction, horizontal direction, one or more diagonal or off axis directions, or combinations thereof.

In yet other forms, the cutting mechanism may include a laser system adapted to pass a laser beam between adjacent trays, or a high pressure nozzle adapted to pass a stream of fluid (e.g. water) between adjacent trays to effect the cutting operation. The laser beam or fluid jet or stream may be applied in a continuous manner over one or more passes across the length of the respective trays until the cutting operation is complete. In other forms, the laser beam or stream of fluid (water) may be applied in pulses, optionally at predetermined intervals of time or selectively via an actuator (e.g. button or trigger) adapted for manual user operation. In certain embodiments, the cutting mechanism may be adapted to perform a vibratory action either directly or indirectly on the plants to facilitate the cutting action, either alone or in combination with one or more other cutting devices or mechanisms.

In some embodiments, the plate or the stack of plates is adapted to fit within a container or vessel, preferably an open top container. The container or vessel is preferably adapted to form a bioreactor for growing the plants. Preferably, the container has a base portion having an open top for releasably receiving a stack of trays therein, and a lid portion which is releasably attachable about the open top of the base, thereby to close the container. Preferably, the lid sealingly engages the base about its open top.

In some embodiments, a sealing element seats between the lid and a periphery of the open top of the base, thereby to enhance the sealing engagement between the lid and the base. Preferably, the sealing element is resiliently compressible. In some embodiments, the lid portion includes a channel extending about its periphery, the channel being adapted to receive the sealing element therein. In some embodiments, the sealing element is in the form of a continuous loop. Preferably, the continuously is configured to correspond to the shape of the shape. In some embodiments, the continuous loop may be generally rectangular in shape, optionally with rounded corners. In some embodiments, the sealing element has a uniform cross-sectional profile of a predetermined thickness. In some embodiments, the thickness of the seal corresponds to approximately half of the depth of the channel, whereby a first (lower) half of the seal is received in the channel associated with the base portion, and a second (upper) half of the seal is received in the channel associated with the lid portion of the bioreactor.

In some embodiments, the base portion and the lid portion of the bioreactor have the same shape and configuration. In such embodiments, the base and lid portions may be used interchangeably, which is beneficial in terms of there be no need to identify and position separate portions of a bioreactor within a plant propagating system employing many bioreactors.

In some embodiments, each lid portion has one or more locating elements arranged at or adjacent to a peripheral edge of the open end, thereby to assist in positioning the base portion thereon to close the container/bioreactor and/or maintaining alignment between the base and lid portions. In some embodiments, each base portion has one or more locating elements arranged at or adjacent to a peripheral edge of the open end, thereby to assist in positioning the base portion thereon to close the container/bioreactor and/or maintaining alignment between the base and lid portions. In some embodiments, the or each locating element is a tab projecting proudly of the associated peripheral edge. In some embodiments, the locating element includes a plurality of tabs arranged at predetermined discrete locates about the peripheral edge of the associated lid or base portion. In some embodiments, each lid or base portion includes a pair of tabs, each tab of the pair of tabs being arranged at diagonally opposite corners of the opening.

In some embodiments, the container has at least one port through which a nutrient supply can be charged into and discharged from the container. In some embodiments, the nutrient supply is in a liquid state.

Preferably, the container has a dedicated inlet port through which the nutrient supply can be charged into the container, thereby to promote growth of the plants. In some embodiments, the inlet port is arranged towards an upper region of the container. In some forms, the inlet port may be arranged in the base portion of the container. In other forms, the inlet port may be arranged in the lid portion of the container/ bioreactor. In some embodiments, the container has two or more inlet ports, whereby each inlet port can be used to charge a separate component or ingredient of the nutrient supply into the container. Preferably, the container has at least one dedicated outlet port through which the nutrient supply can be discharged from the container. In some embodiments, the outlet port is arranged towards a lower region of the base portion of the container.

Preferably, the container is configured such that, when a dosage of the nutrient supply is charged to the base portion, the nutrient supply pools at the base of the container, thereby to come into contact with a portion of the plants; e.g. the root system or base of the plants. In some embodiments, the plate or at least the lowermost plate of the stack of plates is positionable within the container such that, in use, a lower or rooted portion of each plant is immersed in, or otherwise comes into contact with, the nutrient supply.

Preferably, the container includes releasable locking mechanism for securely locking the lid portion to the base portion in the closed position, thereby to facilitate the sealing engagement therebetween. In some embodiments, the locking mechanism acts to positively draw the lid and base portions of the container towards each other, thereby to assist in compressing the sealing element, if one is provided, and enhance the sealing effect.

In some embodiments, a media delivery system is provided and adapted to be fluidly connectable to the container for selectively supplying the nutrient supply to an interior of the container (e.g. base portion). In some embodiments, the media delivery system is a gravity feed system. In some embodiments, the media delivery system is a pressure feed system. In some embodiments, the media delivery system includes a combination of both pressure and gravity feed systems.

Preferably, the media delivery system includes a nutrient container for holding a predetermined volume of the nutrient supply or one or more ingredients of the nutrient supply. Preferably, a conduit or supply line is provided to direct the flow of the nutrient supply between the nutrient container and a bioreactor in which the plants are to be grown. The conduit is preferably in the form of a length of a hollow cylindrical tube. The conduit is preferably connectable at its first end to the port of the nutrient container and at its second end to a port associated with the bioreactor such that the nutrient supply can be charged to and/or discharged from the bioreactor, thereby to facilitate a predetermined dosing regimen to promote growth of plants within the bioreactor.

In some embodiments, the dosing regimen may include delivery of a single batch or volume of the nutrient supply to the container, whereby the nutrient supply remains in contact with a portion of the plant (e.g. the base, root system or other portion) of the plants for a predetermined interval of time, optionally the entire duration of the growing period.

In other embodiments, the dosing regimen may be a temporary immersion regimen, wherein a predetermined volume of the nutrient supply is repeatedly charged to the container for a first predetermined discrete interval of time and subsequently discharged from the container for a second predetermined discrete period of time, whereby the charging and discharging of the nutrient supply to and from the container occurs a predetermined number of cycles and/or over a predetermined duration.

In some embodiments, the nutrient container is relatively rigid (e.g. plastic bottle). In some embodiments, the nutrient container is flexible (e.g. flexible bladder or bag). Preferably, an activation mechanism is operatively associated with the nutrient container, the activation mechanism being configured for movement between an active position in which the nutrient supply is forced to be discharged from the nutrient container charged to the container/bioreactor and an inactive position in which the nutrient supply is prevented from flowing to the container. In some embodiments, the activation mechanism is a selectively operable nutrient supply valve in fluid communication with the supply line.

In some embodiments employing a flexible nutrient container, the activation mechanism is adapted to compress or squeeze or otherwise (temporarily) deform the flexible nutrient container in its active position, thereby to force the nutrient supply to flow from the nutrient container to the container via the supply line. In such embodiments, the activation mechanism disengages or at least partially releases its engagement with the flexible nutrient container when the activation mechanism returns to its inactive position such that the nutrient supply is free to return to the nutrient container via the supply line.

In some embodiments, a backflow prevention mechanism such as, for example, a one-way or check valve is associated with the supply line to prevent backflow of the nutrient supply when the activation mechanism is in its inactive position. In some embodiments, when the activation mechanism is in the inactive position, the nutrient supply can freely discharge from the container via the supply line, optionally back to the nutrient container (e.g. in a temporary immersion dosing regimen) or waste.

In some embodiments, a nutrient controller is operatively associated with the media delivery system, the nutrient controller being adapted to facilitate autonomous or semi-autonomous control of the dosing regimen. In some embodiments, a nutrient controller is adapted to facilitate manual user operation and thus selective manual control of the dosing regimen.

In some embodiments, the system includes a carrier for aseptic handling of the plate or stack of plates. Preferably, the carrier is configured such that it can be used to carry a desired number of plates. In some embodiments, the carrier is configured such that it is able to carry the entire stack of plates. For example, the carrier may be adapted to lift and remove the entire stack of trays from the base portion of the bioreactor once the plants growing therein have reached a predetermined stage of development or growth, wherein the removed stack of trays with plants can be positioned such that the cutting (or other desired) operation can be performed on the plants within the stack of plates. In some embodiments, the carrier is configured such that it can be used to carry a group or subset of the entire stack of plates.

In some embodiments, each plate has a lifting formation to facilitate engagement with the carrier. In some embodiments, the lifting formation includes a pair of ridges, notches or openings associated with respective side edges of each plate.

In some embodiments, the carrier includes a handle and a pair of arms extending from the handle, the arms being adapted to engage a tray or stack of trays, whereby movement of the carrier via the handle causes a corresponding movement of the trays for positioning as desired (e.g. for aseptically removing the trays from the container). Preferably, the arms extend downwardly from the handle, thereby in use enabling the arms to extend into the base portion of the container from above and thereafter engage the stack of trays.

In some embodiments, each arm may have a tray engaging formation associated with its distal end. For example, each arm may have a rail or lip extending transversely therefrom (i.e. inwardly towards each other). Preferably, each tray may have an arm engaging formation adapted for engagement with the carrier, thereby to facilitate aseptic handling of the trays. For example, each tray may have a receiving formation such as a cut-out or recess associated with side edges of the respective tray, the receiving formations being adapted to releasably received the rail or lip.

In some embodiments, the pair of arms are biased towards each other, thereby to facilitate engagement with the tray or stack of trays. In some embodiments, an operative member such as a button or trigger is operatively associated with arms, wherein operation of the operative member causes the arms to move away from each other against the action of the biasing mechanism. Preferably, the operative member is selectively operable by a hand or finger of a user.

In some embodiments, the pair of arms are held in fixed spaced apart relation, wherein lifting elements (e.g. lugs, pins, plates, etc) are arranged and configured so as to be movable relative to a respective arm (e.g. via trigger or other user action) to engage at least one tray for lifting one or more trays. The use of fixed spaced apart arms can be particularly advantageous as it prevents and relative movement therebetween during the lifting process and thereby reduces the possibility of releasing or dropping the tray or stack of trays before they have been placed in a desired safe location (e.g. a cutting station or other station or zone employed by the plant propagating system).

In some embodiments, the carrier may include means other than mechanical arms for grasping and moving the trays as described above. For example, in certain embodiments the carrier may include an element for grasping the trays selected from the group including but not limited to: a clamping device, a magnetic device, a suction device, a threaded device and the like.

In some embodiments, a cradle is provided for holding a stack of trays in relative alignment, preferably vertical alignment, whereby the passage defined by the aligned openings of the respective trays is maintained in an open position.

In some embodiments, the cradle includes a floor portion, with a pair of side edge portions extending upwardly therefrom such that the stack of trays can be received therebetween. Preferably, the side edge portions are spaced apart to an extent such that the stack of trays are close fittingly received therebetween, thereby to limit lateral movement of the trays and maintain alignment thereof.

In some embodiments, the cradle includes a backstop against which the stack of trays can abut, thereby to limit the extent of rearward movement of the trays relative to the floor portion of the cradle. In some embodiments, the backstop includes a flange depending transversely from each side edge portion, preferably extending inwardly towards a centre line of the floor portion.

In some embodiments, a raising member is provided for raising a front edge of the floor portion relative to a rear edge thereof, whereby in use the floor portion slopes downward from front to back such that the stack of trays tends to self-position itself against the backstop. Preferably, the raising member is a downwardly depending front lip edge associated with the front edge of the floor portion.

In some embodiments, the floor portion includes a friction reducing element for reducing friction between the stack of trays and the floor portion, thereby to facilitate ease of relative translational sliding movement of the stack of trays across the floor portion and thus helping to maintain alignment of the stack of trays when transferring the trays to and from the cradle. For example, the friction reducing element may include one or more, preferably at least two, raised friction reducing rails projecting above the upper surface of the floor portion. Preferably, the floor portion has a pair of parallel friction reducing rails.

In some embodiments, a divider plate is provided for dividing the stack of trays into smaller sub-stacks after the cutting operation. Preferably, the divider plate is formed as a thin plate structure such that it can slide between a pair of adjacent vertically stacked trays, thereby forming a platform to assist in lifting a sub-stack of trays off the initial stack.

According to another aspect of the invention, there is provided a system for delivering a nutrient supply to growing plants, the system including:

a nutrient container for holding a predetermined volume of the nutrient supply; and an activation mechanism operatively associated with the nutrient container, whereby operation of the activation mechanism causes at least a portion of the nutrient supply to flow from or to the nutrient container.

Preferably, the nutrient supply is in a liquid state, whereby it can be readily controlled to flow to and from the nutrient container as required. In some embodiments, the nutrient supply may form one ingredient of a nutrient supply mixture, wherein it can be combined with one or more other ingredients of the nutrient supply mixture in accordance with a predetermined ingredient dosage ratio.

The system is particularly advantageous for use in delivering a liquid nutrient supply to plants being grown under plant tissue culture (PTC). The system will be described therefore, by way of example only, with reference to such PTC applications. However, the system has potential for broader application and can be readily adapted for use in a variety of other systems, processes and arrangements for growing plants.

In particular, the present system can be advantageously configured for use in systems for growing various plant types. For example, the system can be used to deliver a nutrient supply under a predetermined dosing regimen to actively promote growth of various types of plants including, but not limited to, arborescent plants and acaulescent plants. Arborescent plants are commonly referred to as tree-like plants, normally having a single stem or trunk. Acaulescent plants typically have little or no stem above ground or soil level, sometimes being referred to as tufted or rosette type plants.

A selectively controllable valve is preferably operatively associated with the port, thereby to effectively open and close the port and thus control the flow of the nutrient supply. Preferably, the valve is selectively operable between a first or open state in which the nutrient supply can flow through the port (either in or out) and a second or closed state in which the nutrient supply is prevented from flowing through the port (either in or out).

In some embodiments, the valve is configured to be manually operable, whereby hand operation of a user is required to move the valve between its first (open) and second (closed) states. In some embodiments, the valve is operatively associated with a control unit, thereby to enable autonomous or semi-autonomous control of the valve between its first (open) and second (closed) states. In some embodiments, the control unit may include a variety of interconnected electronic and pneumatic components which operate to selectively open and close the valve. For example, the control unit may be configured to operate the valve on the basis of a predetermined logic algorithm based on, but not limited to, set times of the day, predetermined timed intervals, user activation or input, the output of one or more sensors which are adapted to sense the amount of nutrient fluid in a bioreactor or other vessel or within the nutrient container, or sense a particular parameter of a growing plant or plants (e.g. size—height or width), etc. In some embodiments, the valve may not be present.

In some embodiments, the bioreactor port is formed in a side wall of the bioreactor. In some embodiments, the bioreactor port is formed in an upper portion of the side wall of the bioreactor. In some embodiments, the bioreactor port is formed in a lower portion of the side wall of the bioreactor. In some embodiments, the bioreactor port is formed in a base or floor of the bioreactor. In some embodiments, the bioreactor port is formed in a top wall of the bioreactor. In some embodiments, the bioreactor port is formed in a cap, cover or lid of the bioreactor.

In some embodiments, the first end of the conduit is releasably connectable to the port of the nutrient container. In some embodiments, the first end of the conduit is fixedly connected to the port of the nutrient container.

In some embodiments, the second end of the conduit is releasably connectable to the port of the bioreactor. In some embodiments, the second end of the conduit is fixedly connected to the port of the bioreactor.

In some embodiments, the second end of the conduit has, or has a fitting with, two or more end connectors, thereby to facilitate connection with two or more bioreactors such that the nutrient supply can be fed to each bioreactor substantially simultaneously. Preferably, a separate nutrient container is used to provide a dedicated nutrient supply to each bioreactor.

Preferably, the activation mechanism is operatively associated with the nutrient container, the activation mechanism being configured for movement between an active position in which the nutrient supply is forced to be charged to the container and an inactive position in which the nutrient supply is prevented from flowing to the container. In some embodiments, the activation mechanism includes a selectively operable nutrient supply valve in fluid communication with the conduit or supply line.

In some embodiments, the nutrient container is relatively rigid (e.g. plastic bottle). In such embodiments, the activation mechanism may be in the form of a piston movably arranged within the container, whereby movement of the piston in a first direction causes at least a portion of the nutrient supply to flow from the container and movement of the piston in a second direction can cause at least a portion of the nutrient supply to flow into the container. Preferably, the piston is configured for selective sliding movement along the longitudinal axis of the nutrient container.

Preferably, the nutrient container is flexible (e.g. flexible bladder or bag) such that, when a compressive force is applied to the nutrient container, at least a portion of the nutrient supply is discharged from the nutrient container via its port, whereby it can be directed to a bioreactor to promote growth of plants therein. The compressive force may be applied directly or indirectly to the nutrient container.

In some embodiments employing a flexible nutrient container, the activation mechanism is adapted to compress or squeeze or otherwise (temporarily) change or deform the flexible nutrient container in its active position, thereby to force the nutrient supply to flow from the nutrient container to the container via the supply line. In such embodiments, the activation mechanism disengages or at least partially releases its engagement with the flexible nutrient container as or when the activation mechanism returns to its inactive position such that the nutrient supply is free to return to the nutrient container via the supply line.

In some embodiments, a backflow prevention mechanism such as, for example, a one-way or check valve is associated with the conduit or supply line to prevent backflow of the nutrient supply when the activation mechanism is in its inactive position. In some embodiments, when the activation mechanism is in the inactive position, the nutrient supply can freely discharge from the container via the supply line, optionally back to the nutrient container (e.g. in a temporary immersion dosing regimen) or waste.

Preferably, the nutrient container is arranged in use at a level below that at which the bioreactor is located, thereby to enable at least a portion of the nutrient supply within the bioreactor to return to the nutrient container, preferably via the same conduit, under gravity.

In other embodiments, the nutrient container is movable from a first position below that at which the bioreactor is located below, or at least below the bioreactor port, wherein the nutrient supply can freely flow from the bioreactor to the nutrient container, and a second position in which the bioreactor is located above, or at least above the bioreactor port, wherein the nutrient supply can freely flow from the nutrient container to the bioreactor. In such embodiments, the activation mechanism may be adapted to selectively raise and lower the nutrient container. For example, the activation mechanism may include a liner actuator, robotic arm or other positioning mechanism for raising and lowering the nutrient container, as required. In some embodiments, the activation mechanism may be configured to raise and lower two or more nutrient containers. In other forms, the activation mechanism may be adapted to selectively raise and lower the bioreactor, or group of two or more bioreactors, relative to the nutrient container. In some forms, the activation mechanism may be adapted to change the position of both the nutrient container and the associated bioreactor.

In some embodiments, the activation mechanism may include a force applying element or mechanism. In some embodiments, the force applying element includes a substantially rigid member which can be brought into contact with the nutrient container to apply a compressive force thereto. In some embodiments, the nutrient container is positioned on or against a substantially rigid surface, wherein the nutrient container located between the rigid surface and the rigid member of the activation mechanism such that the compressive force can be applied to the nutrient container by movement of the rigid member relative to the rigid surface.

In some embodiments, the force applying element or mechanism of the activation member includes a gripper or jaw-type device which is selectively operable between open and closed positions, whereby upon movement towards the closed position the gripper or jaw-type device applies a compressive force to the nutrient container to cause at least a portion of the nutrient supply to flow out of the nutrient container via the port. In some embodiments, the gripper may include a pair of hingedly connected jaws, the jaws being movable between the open and closed positions.

In some embodiments, the activation mechanism includes an actuator for controlling movement of the force applying element or mechanism. The actuator may be a linear actuator, robotic arm or the like.

In some embodiments, the activation mechanism includes an inflatable element such as, for example, an inflatable bag, bladder or pillow. Preferably, the inflatable element of the activation mechanism is arranged in use such that, upon inflation (i.e. a change in configuration from a deflated or partially/semi-deflated configuration to an inflated or more inflated configuration) it bears against the nutrient container, thereby to apply a compressive force to the nutrient container which causes a corresponding change to the configuration of the nutrient container such that at least a portion of the nutrient supply flows out of the nutrient container via its port. The inflatable element may directly or indirectly bear against the nutrient container to apply the compressive force.

In some embodiments, the inflatable element is configured to bear against a single nutrient container, thereby to independently control the flow of nutrient supply into and out of the respective nutrient container.

In some embodiments, the inflatable element is configured to bear against a plurality of nutrient containers substantially simultaneously, thereby to control the flow of nutrient supply into and out of each nutrient container. Such a configuration is particularly advantageous for use in a system employing multiple bioreactors in which the plants grown in each bioreactor are the same, at the same stage of development and/or otherwise require the same dosing regimen.

In some embodiments, the inflatable element of the activation mechanism includes at least one receiving formation for releasably receiving at least one nutrient container. In some embodiments, the receiving formation is a pocket. In some embodiments, the inflatable element includes two or more pockets. In some embodiments, each pocket may be configured to receive a single nutrient container. In some embodiments, each pocket may be configured to receive two or more nutrient containers.

In some embodiments, one or more pockets may be formed as an external pocket of the inflatable bladder of the activation mechanism. In some embodiments, one or more pockets may be formed as an internal pocket of the inflatable bladder of the activation mechanism.

In some embodiments, one or more pockets may include a window, thereby to permit visual inspection of the nutrient container received therein. In some embodiments, one or more pockets may be formed of a transparent (flexible) material.

In some embodiments, each pocket has a single opening for inserting the nutrient container therein (and removing therefrom). In some embodiments, each pocket has a single opening in a side end of the pocket or a top edge of the pocket. In some embodiments, each pocket has two openings (e.g. at both side ends) for inserting the nutrient container therein (and removing therefrom). The use of two openings can be advantageous to enable a user to manipulate the nutrient container and/or pocket with two hands when inserting and removing the nutrient container.

In some embodiments, the or each pocket is formed as a flap, the flap being secured along one edge (e.g. a lower edge) to the bladder (e.g. a side wall of the bladder) and releasably securable along an opposing edge (e.g. an upper edge) to the bladder (e.g. the side wall of the bladder), wherein the opposing edge can be released to allow insertion and removal of the nutrient container and secured to retain the nutrient container within the pocket. In some embodiments, a releasably securable closing mechanism is configured to facilitate opening and closing of the pocket. The releasably securable closing mechanism is preferably associated with the opposing free edge of the flap. In some embodiments, the releasably securable closing mechanism includes hook and loop fasteners (e.g. Velcro®), snap-lock fasteners, press buttons/studs, zippers, buttons or the like. Preferably, a first portion of the releasably securable closing mechanism is connected to the free edge of the flap and a second portion is connected to the bladder, wherein selective movement of the flap can bring the first and second portions of the releasably securable closing mechanism into mating engagement to hold or secure the free edge relative to the side wall of the bladder and thereby close the pocket.

In some embodiments, the inflatable bladder of the activation mechanism is connectable to a pressurised fluid (air or liquid) supply, whereby the pressurised fluid supply is selectively operable to inflate and deflate the inflatable bladder as desired.

In some embodiments, the system is configured to deliver the nutrient supply in accordance with a predetermined dosing regimen. In some embodiments, the dosing regimen may include delivery of a single batch or volume of the nutrient supply to the container, whereby the nutrient supply remains in contact with a portion of the plant (e.g. the base, root system or other portion) for a predetermined interval of time, optionally the entire duration of the growing period.

In other embodiments, the dosing regimen may be a temporary immersion regimen, wherein a predetermined volume of the nutrient supply is repeatedly charged to the container for a first predetermined discrete interval of time and subsequently discharged from the container for a second predetermined discrete interval of time, whereby the charging and discharging of the nutrient supply to and from the container occurs a predetermined number of cycles and/or over a predetermined duration. In some embodiments, the first predetermined discrete interval of time is less than the second predetermined discrete interval of time. For example, the nutrient supply may be fed to the bioreactor and held therein for a period of approximately 15, 30, 45 or 60 minutes per 24-hour period. Such embodiments can be useful in enhancing the rate of plant growth, reducing the risk of contamination and reducing the quantity of nutrient that is required over a growing period. In some embodiments, the first predetermined discrete interval of time is greater than the second predetermined discrete interval of time. In some embodiments, the first predetermined discrete interval of time is equal to the second predetermined discrete interval of time.

In some embodiments, a housing is provided for releasably housing one or more nutrient containers. In some embodiments, the housing includes a plurality of discrete chambers in which one or more nutrient containers can be received. Preferably, each chamber is sized to receive a single nutrient container. In some embodiments, the housing includes a generally elongate rectangular prismatic body with a plurality of dividers arranged to form the respective chambers. Preferably, the body of the housing is an opened top construction, having a floor, side walls and end walls.

Preferably, the housing is resiliently deformable such that in use the activation mechanism may be adapted to releasably deform or squeeze the housing so as to cause a corresponding compression or squeezing force to be applied to each of the nutrient containers within the housing, thereby to cause the nutrient supply of each respective nutrient container to be discharged via the respective port.

In some embodiments, the magnitude, rate and/or duration at which the compressive force is applied, either directly or indirectly, to the nutrient containers is controllable such that the flow rate of the nutrient supply to and from the nutrient supply can in turn be similarly controlled. In some embodiments, the discharge flow rate may vary from the charging flow rate. In some embodiments, the charging and discharge flow rates may be substantially the same.

According to another aspect of the present invention, there is provided a plant propagation system, including:

a tray having at least one plant receiving opening for receiving a growing plant; and a cutting element adapted to make at least one cut in the plant, thereby to divide the plant into two or more plant portions.

This aspect of the disclosure is particularly well suited and advantageous for use with acaulescent (tufted or rosette) plants. As foreshadowed, acaulescent plants is understood to include plants which typically have little or no stem above ground or soil level. Accordingly the cutting element is preferably configured to enable it to make a cutting action (downwardly) along a vertical axis.

Preferably, the cutting element is configured to cut or divide each plant evenly, whereby each cut plant portion is of substantially the same size. Preferably, the cutting element is configured in use to cut through the central point of the respective opening in the tray, thereby to facilitate cutting the plant into equally sized cut plant portions. In some embodiments, the cutting element is adapted to cut each plant into a predetermined number of smaller plant portions; for example, but not limited to, two, three, four, five, six, seven or eight portions. In some embodiments, the cutting element is adapted to cut each plant in half, thereby to produce two plant portions of substantially the same size. In various embodiments, it is preferred to use the cutting element to divide each plant into four substantially equal sized portions or, in other words, to quarter each plant.

In some embodiments, the cutting element is adapted to divide each plant into the predetermined smaller plant portions in a single cutting action. In some embodiments, the cutting element is adapted to divide each plant into the predetermined smaller plant portions with two or more cutting actions, strokes or passes. For example, subject to the shape and configuration of the cutting element, the cutting element may be employed to cut or divide the plant in half under a first cutting action. After the first cutting action, in this example, the blade may be turned relative to the tray by a predetermined extent or angle (e.g. 90 degrees) such that the cutting element can make a second cutting action to further divide the plant (e.g. cut each of the half plant portions formed by the first cutting action into quarter plant portions). In some embodiments, the tray may be moved (e.g. rotated) relative to the blade so as to position the blade relative to the tray/plants for the second cutting action. In some embodiments, the blade and the tray are both moved relative to each other after the first cutting action, thereby to position the blade for the second cutting action.

In some embodiments, the cutting element includes a blade. In some embodiments, the blade has a single cutting edge. In some embodiments, the cutting element includes multiple blade elements, wherein each blade element is adapted to fit within a respective opening of a tray for cutting a respective plant located therein. In some embodiments, the cutting edge may include a bevel or chamfer, thereby to enhance its cutting ability in terms of strength of cut (e.g. cutting thicker and/or tougher plants) and/or coarse of cut/accuracy (e.g. fine to coarse cutting). In some embodiments, the cutting edge may be straight-edged, serrated, saw-toothed or the like. In some embodiments, the cutting edge may be adapted to cut the respective plant, or plant portion, with its cutting edge arranged generally parallel to the surface of the tray, or media in which the plant is growing, throughout the cutting action.

For example, where the tray is generally horizontally arranged, the cutting edge may be substantially parallel to the upper surface of the tray and such that the cutting edge is similarly horizontally arranged. In such arrangements, the cutting action of the cutting element may be achieved by moving the cutting element downwardly towards the tray until it engages the plant, whereby further downward movement of the cutting element causes the cutting element to cut or divide the plant into smaller sub-plant portions. In other embodiments, the tray may be movable, thereby to position it and thus the plants in a desired position relative to the cutting element.

In some embodiments, the cutting element may be configured such that it is angled relative to the tray such that during the cutting action the cutting edge progressively engages the plant, thereby to cut or divide the plant into smaller plant portions.

In some embodiments, the cutting edge is shaped or configured to cut or divide the plant into three or more sub-plant portions in a single cutting action.

For example, the cutting element may be generally Y-shaped, thereby to cut or divide the plant into three plant portions. In such embodiments, the angle between the respective arms of the Y-shaped blade is substantially equal (e.g. approximately 120 degrees between each pair of arms), thereby to facilitate cutting of the plant to form three substantially equally sized plant portions.

In other embodiments, the cutting element may be generally t- or plus-sign or '+' shaped, thereby to cut or divide the plant into four plant portions. In such embodiments, the angle between the respective arms of the t- or '+'-shaped blade is substantially equal (e.g. approximately 90 degrees between each pair of arms), thereby to facilitate cutting of the plant to form four substantially equally sized plant portions. In other forms, a single cutting blade may be used to produced four separate cuts in order to divide the plant into four quarter plant portions. For example, a first cut at a 12 o'clock position, a second cut at a 3 o'clock position, a third cut at a 6 o'clock position, a fourth cut at a 9 o'clock position.

It will be appreciated that the cutting element is not limited to having a cutting blade as shaped according to the above non-limiting exemplary forms which have been provided by way of example only. Rather, the cutting element may be configured to cut or divide the plant to form plant portions of a predetermined shape and/or size, including plants portions of differing size and/or shape via a single cutting action.

In some embodiments, the cutting element includes a handle portion extending away from the blade, thereby to facilitate hand manipulation of the cutting element and manual cutting of plants growing within the tray. In some embodiments, the cutting element is adapted to be attached to a selectively operable actuator, thereby to facilitate autonomous and semi-autonomous cutting processes.

In some embodiments, the actuator is adapted to facilitate movement of the cutting element towards and away from the tray, thereby to cause the cutting action for cutting or dividing the respective plant or plants growing within the tray. In some embodiments, the actuator is a linear actuator configured to cause corresponding linear movements (e.g. upward and downward movement) of the cutting element. In some embodiments, the actuator may include a first actuator for effecting linear positional movement of the cutting element and a second actuator for effecting rotary positional movement of the cutting element, thereby to facilitate positioning and alignment of the cutting element relative to the tray and thus the respective plant growing therein. In some embodiments, the cutting element may form the end effector of a robotic arm, whereby the robotic arm is configured to control movement of the cutting element and thus the associated cutting action including, for example, cutting speed, frequency, timing, etc.

Preferably, the tray includes a plurality of plant receiving openings. In some embodiments, each tray has a predetermined profile or shape. In some embodiments, each tray is generally rectangular, square, triangular, circular, hexagonal or other suitable polygonal shape. Preferably, each tray has a generally uniform thickness or height.

Each opening is preferably configured to suit a particular plant type or size intended to be grown therein. In some embodiments, each plant receiving opening has the same shape or configuration. In some embodiments, each plant receiving opening is the same size. In some embodiments, the tray includes plant receiving openings of different sizes. In some embodiments, each opening is rectangular, square, triangular, circular, hexagonal or other suitable polygonal shape.

For example, the tray may have a first group of plant receiving openings (two or more) with a first configuration, and a second group plant receiving openings (two or more) with a second configuration, wherein the plant receiving openings of the first configuration is different to the second configuration. In some embodiments, the openings of the first group may have the same shape as those of the second group but be of a different size.

In some embodiments, each plant receiving opening is a through opening. In some embodiments, each plant receiving opening is an open-topped opening or cavity. Each open-topped opening or cavity preferably has a floor. Preferably, the floor is perforated with one or more openings, thereby to facilitate feeding of a nutrient supply to a root system of the plant growing within the respective opening. In some embodiments, the floor of each opening may be defined by a separate floor piece extending across, or adjacent to, the bottom or lower end of each respective plant receiving opening. In some embodiments, a single floor piece may extend across the lower surface of the tray, thereby to define the floor portion of each plant receiving opening.

Preferably, each plant receiving opening is adapted to receive a single plant, more preferably an acaulescent type plant.

In some embodiments, the plurality of plant receiving openings are arranged in a regular array (e.g. square or rectangular array), preferably with regular/even spacing between the openings. In some embodiments, the openings in each tray are arranged in a polar array. In some embodiments, the plurality of plant receiving openings are arranged in an irregular array. In some embodiments, the openings may be arranged to form an offset array wherein alternate rows are staggered by a predetermined extent (e.g. 50% of the opening size), thereby to enable a reduced spacing between adjacent openings and thus the provision of additional openings per plate.

Preferably, each tray is configured such that it can be received in a plant growing vessel or bioreactor. Preferably, each tray is configured such that it can rest freely on the base of the bioreactor, thereby in use to facilitate feeding of the plants via a liquid nutrient supply pooling on the base of the bioreactor.

In some embodiments, the floor of each plant receiving opening acts or bears against the lowerside of the respective plant, thereby to limit movement of the plant during the cutting action. In other embodiments, the base of the bioreactor bears against the lowerside of the respective plant, thereby to limit movement of the plant during the cutting action.

In some embodiments, a single cutting element is used to cut each plant growing in the tray. For example, the cutting element may be employed to perform a cutting action in each opening of the tray according to a predetermined routine (e.g. successively across the first row, then the second row and so on). In some embodiments, the cutting element is used to perform the cutting action on a plant by reference to a predetermined growing period of each plant or development stage (e.g. size or shape) of each plant.

In some embodiments, the cutting element may be adapted to cut a plurality of plants during a single cutting operation. In some embodiments, the cutting element may include a plurality of blades arranged in relative spaced apart relation, wherein the spacing between blades corresponds to the spacing between the openings of the tray in which simultaneous cuts is desired. For example, the blades may be spaced apart such that each plant in a first row of the tray is cut simultaneously. In other forms, two blades are used to simultaneously cut two plants. In some embodiments, the blades may be spaced apart so as to cut plants in every second, third, fourth or fifth opening of a row of the tray or across different rows of the tray. In some embodiments, the cutting element may be adapted to cut each plant growing within a plant receiving formation of the tray simultaneously.

In some embodiments, each tray has a cover. Preferably, each cover is releasably mountable to the respective tray, preferably the upper surface of the tray. In some embodiments, the cover is mounted to the tray to constrain or limit the height to which each plant can grow. In some embodiments, the cover has one or more openings through which one or more shoots of the respective plants can grow. In some embodiments, the cover is adapted to cut or trim the plants upon removal of the cover from the tray such that each trimmed plant has substantially the same height. For example, the cover may be slidably mounted to the tray, whereby upon sliding action to remove the cover from the tray, the tray shears the plants to trim the shoots projecting above the height of the cover.

In some embodiments, a plurality of acaulescent (tufted) plants can be arranged and grown in a first tray positioned within a bioreactor, wherein a second tray can be placed or stacked on the first tray to enable a lateral cutting element to be passed between the first and second trays, thereby to cut the leaves and thus trim the height of the acaulescent plants. Preferably, the lateral cutting of the leaves is performed before making the vertical cutting action to split or divide the acaulescent plants into the respective plant portions.

Preferably, the system includes a plurality of trays wherein a first tray can be used to grow a first batch of plants, and a second tray can be used to grow a second batch of plants from plant portions cut from the first batch of plants. Third and further trays can be used to grow additional batches from the cut plant portions. This process can be repeated to continue the growing cycle.

In some embodiments, the cutting element is held in place, within the respective plant receiving opening, at the end of the cutting action whilst the cut plant portions are removed from the cavity/tray. By retaining the cutting element in this position during removal of the cut plant portion, there is a reduced risk of inadvertently removing another of the cut plant portions during the extraction process.

In some embodiments, the extraction of the cut plant portions is a manual operation, optionally performed by hand or with the aid of a dedicated plant grasping mechanism. In some embodiments, the grasping mechanism may be attached to an actuator such as for example, a linear actuator, a rotary actuator or a robotic arm, to facilitate autonomous or semi-autonomous removal of the cut plant portions from the tray and subsequent transfer to another tray to recommence the growing process.

In some embodiments, the grasping mechanism may be in the form of tongs, tweezers, pincers, pliers or the like. Such grasping mechanisms preferably include a pair of mutually opposable clamping arms which are biased away from each other to an open position, wherein selective closing force applied to the clamping arms moves the arms relative to one another to close the opening between the arms and thereby to grasp a cut plant portion, in use.

In some embodiments, the grasping mechanism includes a suction or vacuum device for grasping, lifting and moving the cut plant portions. Such grasping mechanisms may include a hollow tube, optionally with a suction cup fitted to one end (e.g. free end). Preferably, a selectively operable air supply is connected to the other end of the hollow tube, the air supplying being configured to produce a negative pressure within the tube for lifting a cut plant portion. In some embodiments, the negative pressure is turned off to release the cut plant portion for placement in a desired location (e.g. another tray). In some embodiments, the air supply is selectively operable to produce a positive pressure within the hollow tube to assist in releasing the cut plant portion from the free end of the tube for placement in the desired location. In certain embodiments, the suction or vacuum grasping mechanism may include a first tube for grasping the cut plant portions under negative pressure, and a second tube for releasing the cut plant portions from the tube under a positive pressure (e.g. a puff of air).

Preferably, when an acaulescent plant is divided by a vertical cut into smaller plant portions, at least one plant portion is left within the respective opening of the tray in which the plant was grown such that the tray can be returned to a bioreactor to recommence a growing cycle of the retained plant portions, whilst the other portion or portions are extracted and placed in another tray to provide a new batch of plant portions to be subjected to a growth cycle.

According to another aspect of the present invention, there is provided a plant propagation system including:

a body for receiving at least one growing plant; and a cutting element adapted to make at least one vertical cut in the plant, thereby to divide the plant into two or more plant portions such that each plant portion can be replanted or repositioned (e.g. in another tray) for further growth.

According another aspect of the present invention, there is provided a method of propagating plants, the method including the steps of:

providing at least one plant receiving opening;

placing a plant into the or each plant receiving opening, the plant being at a first predetermined stage of development;

feeding the plant with a nutrient supply according to a predetermined feeding routine; and cutting the plant along a substantially vertical axis once it reaches a second predetermined stage of development, thereby to divide the plant into two or more plant portions such that each plant portion can be replanted or repositioned (e.g. in another tray) for further growth.

BRIEF DESCRIPTION OF THE FIGURES

Embodiments of the present disclosure will now be described, by way of example only, with reference to the accompanying drawings in which:

FIGS. 1A to 1C show a perspective view, front view, and ride side view respectively of an embodiment of a bioreactor according to the present disclosure, with the lid in a closed position;

FIGS. 2A to 2C show a perspective view, front view, and ride side view respectively of a base of the bioreactor of FIG. 1;

FIGS. 3A and 3B show a perspective view and a right side view of an embodiment of a stackable tray for holding and growing a plurality of plants in relative spaced apart relation;

FIGS. 13A, 13B, and 13C shows a schematic diagram of another embodiment of a media delivery system according to the present disclosure in a first state with a liquid nutrient supply charged to the bioreactor; a second state with the liquid nutrient supply charged to the bioreactor; and a third state with the liquid nutrient supply ready to be charged to the bioreactor, respectively;

FIG. 16 shows representative cut lines along which each plant growing in the tray of FIG. 1 is cut so as to produce four cut plant portions of substantially the same size; and FIG. 17 shows a schematic representation of the process of transferring each of the cut plant portions to another tray to recommence the growing process.

DETAILED DESCRIPTION

Figure 4:
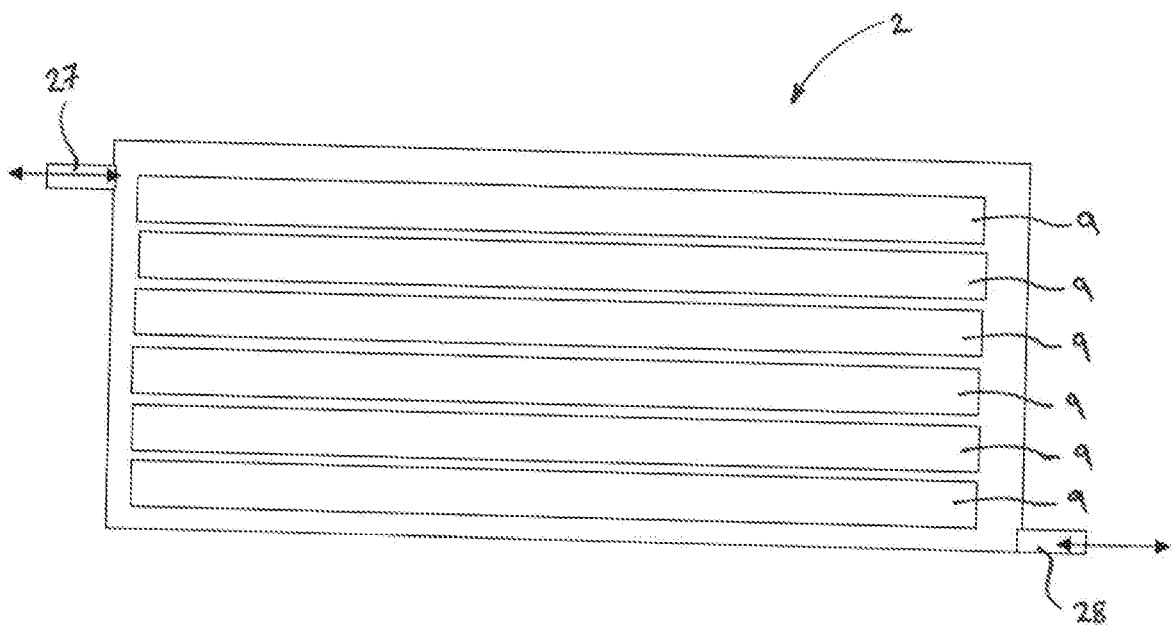
FIG. 4 shows a schematic side view of an embodiment of a bioreactor with a stack of trays nested therein.
Figure 5:
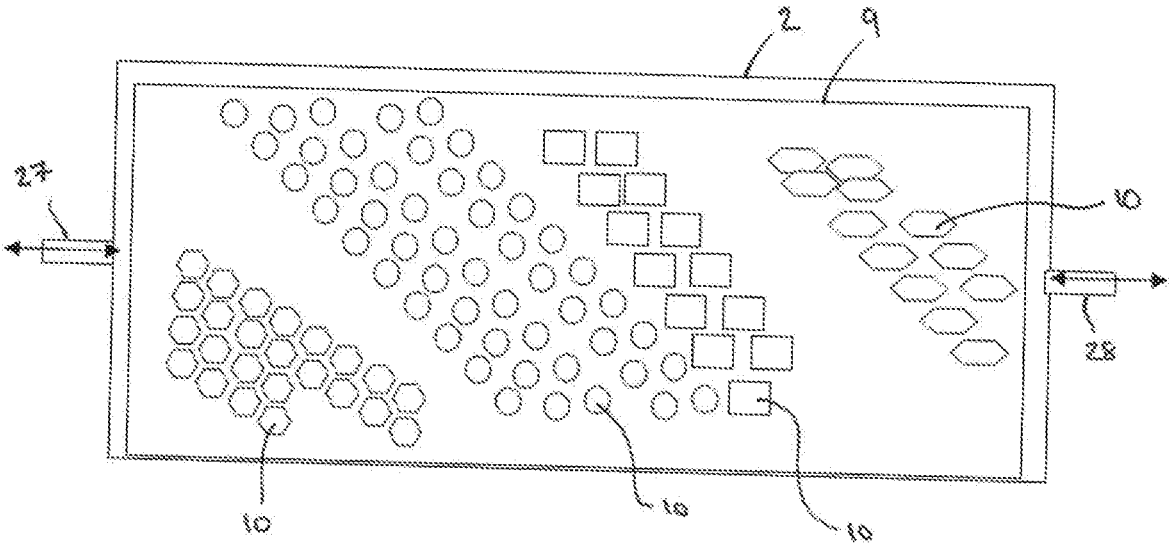
FIG. 5 shows a top view of an embodiment of a bioreactor showing various exemplary shapes, configurations and layouts of openings within a stackable plant growing tray.

Referring to the drawings and initially to FIGS. 1A-C, an embodiment of a plant propagation system 1 for growing plant tissue culture is shown.

The system 1 includes a container in the form of a bioreactor 2 for growing the plant tissue culture. As clearly illustrated in FIGS. 1A and 2C, the bioreactor 2 has a base portion 3 with an open top 4. A lid portion 5 is releasably attachable about the open top 4 of the base portion 3, thereby to close the bioreactor such that a suitable sterile environment is provided for growing plants therein. Preferably, the lid portion 5 sealingly engages the base portion 3 about its open top 4.

To enhance the seal between the base portion 3 and lid portion 5, a sealing element in the form of a continuous uninterrupted resiliently compressible sealing element (not shown) is adapted to sit between the lid portion 5 and a peripheral edge 6 of the open top 4 of the base portion 3. The base portion 3 and/or lid portion 5 preferably includes a channel 7 extending about the periphery of its opening, wherein the channel 7 is adapted to receive the sealing element therein. An exemplary form of such a channel 7 formed in the base portion 3 is shown in FIG. 2A.

The bioreactor container 2 includes releasable locking mechanism for securely locking the lid portion 5 to the base portion 3 in a closed sealed configuration as shown in FIG. 1. In the illustrated embodiment, the locking mechanism is in the form of six manually operable latches 8 which are configured to positively draw the lid and base portions (3, 5) of the bioreactor 2 towards each other, thereby to assist in compressing the sealing element therebetween. It is appreciated that any number of latches 8 may be used to secure the base portion 3 and the lid portion 5 toward each other.

Referring now to FIGS. 3 and 4, the base portion 3 is configured for releasably receiving a holder for holding at least two plants in relative spaced apart relation. In the exemplary form of FIG. 3, the holder is in the form of a generally rectangular tray 9 having a plurality of openings 10 arranged in a predetermined ordered pattern. This is a particular advantage over existing plant tissue culture systems where the plants are typically placed and grown in a randomly spaced arrangement across the area of the base of the bioreactor.

In the exemplary form of FIG. 3A, each opening 10 is hexagonal in shape. It will be appreciated that the use of such hexagonal openings 10 enables the openings to be arranged in relative close proximity to each other, with successive rows overlapping to a predetermined degree. This close-fitting arrangement of the openings 10 thus enables a greater number of openings 10 to be formed in the tray 9, thereby enhancing the overall efficiency of propagating plant tissue cultures via the plant propagation system 1. Advantageously, each opening 10 is dedicated to receiving a portion of a single plant.

It will be appreciated that the openings 10 are not limited to the illustrated hexagonal shape, rather the openings may be any suitable shape including but not limited to circular, oval, square, rectangular, triangular, and other polygonal shapes.

To further enhance the efficiency of the plant propagation system 1 and as shown in FIG. 4, in some examples, it may be desired that a plurality of trays 9 are provided and configured so as to be stackable. FIG. 4 shows a schematic representation of a tower or stack of trays 9 positioned within the bioreactor 2.

Each tray 9 preferably has the same or similar shape and/or configuration. It will be appreciated that the ability to arrange two or more trays of similar configuration in a vertical tower or stack advantageously allows the respective openings 24 to be aligned such that a plurality of through passages of a predetermined height appropriate for a particular plant type can be formed or constructed, whereby a plant can grow upwardly through each passage.

The stack of trays 9 offers several advantages for enhancing operational efficiency, including providing a support for each plant as it height increases over the growing period, and guiding each plant upwardly in a generally vertical direction.

The use of a stack of trays 9 also enables the plants to be grown to a greater height such that multiple cuts can be made to the stem of each plant, thereby significantly increasing the number of plants that can be produced from a single batch bioreactor. For example, in a stack of, say, four trays where each tray 9 has fifty openings, if a cut is made between the middle two trays 9 there will be provided two batches of plants each having fifty cuttings and thus 100 cuttings in total. If, for example, the stack was increased to, say, six trays and a cut was made between every second tray, this would produce three batches of fifty cuttings and thus 150 cuttings in total. It will therefore be appreciated that there is correlation between the overall efficiency of the plant propagation system 1 and both the number of openings per tray 9 and the number of cuts that can be made to each plant.

The above arrangements are merely provided by way of example to demonstrate the operational efficiencies that can be gained from the plant propagation system 1. In practice, at least the lowermost tray 9 may be used to support the root system of the plants towards the floor of the base portion 3 of the bioreactor 2 and thus may not be used to produced cuttings for regrowth; this being reserved for the upper trays within the stack. It is also to be appreciated that the sub-stacks are not intended to be limited to pairs of trays 9 as described above, rather any suitable number of trays to provide the sub-stack with a height substantially corresponding to the desired height of the cuttings to be produced may be selected. For example, the sub-stacks may include three, four, five, six, seven, eight, nine, ten, or more trays. Thus, the stack of trays may include an even number of trays or an odd number of trays 9 as desired.

Thus it is will be appreciated that the cutting action afforded by the present system is particularly well suited to and provides advantages in relation to arborescent type plants. Such plants are referred to as tree-like plants, normally having a single stem or trunk.

It will be appreciated that the ability to grow multiple plants in an orderly spaced array and such that the height of each plant is substantially the same over the growing period, advantageously enables each cutting operation to be performed on each plant within the holder over a single pass. The efficiencies that can be realised from the ability to cut multiple plants over a single pass far exceeds the efficiency, or lack thereof, of systems in which individual plants are cut one at a time.

Each tray 9 preferably has a uniform thickness at least across the main (or central) area in which the openings 10 are formed. In the illustrated embodiment as best seen in FIG. 3B, each tray 9 includes one or more end projections 11 of reduced thickness, thereby to facilitate selection and removal of a desired tray or sub-set of trays from the stack of trays and/or to provide a lead-in opening between pairs of trays 9 to facilitate performing a cutting operation between adjacent trays within the stack of trays.

In this regard, it is preferred that no locating elements are formed on the trays 9 such that there is no obstruction extending between adjacent trays 9, thereby enabling the cutting operation to be performed freely between a pair of adjacent trays 9. Rather, the bioreactor 2 or more specifically the base portion 3 of the bioreactor 1 is configured to locate and support the tray 9 or stack of trays 9 in alignment. In some forms, the side walls of the base portion 3 may act to provide the necessary support to the stack of trays 9. In other forms, one or more locating elements such as, for example, raised ribs or lugs may be formed on the floor of the base portion 3 to support and locate at least the lowermost tray 9 of the stack.

Figure 7:
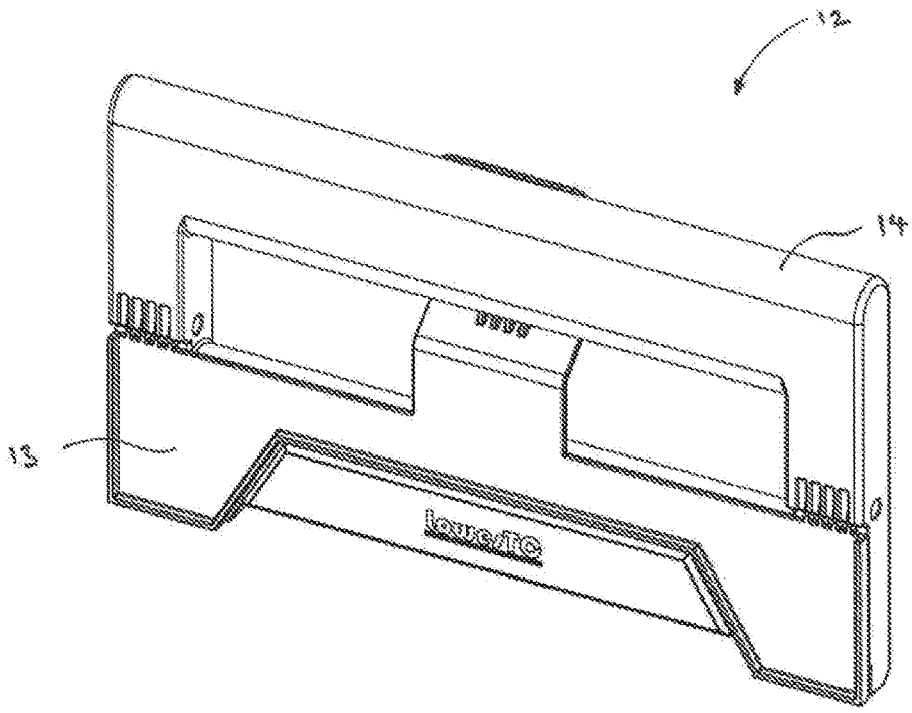
FIG. 7 shows a perspective view of an embodiment of a hand-tool for releasably holding and manoeuvring a cutting/divider plate.
Figure 8:
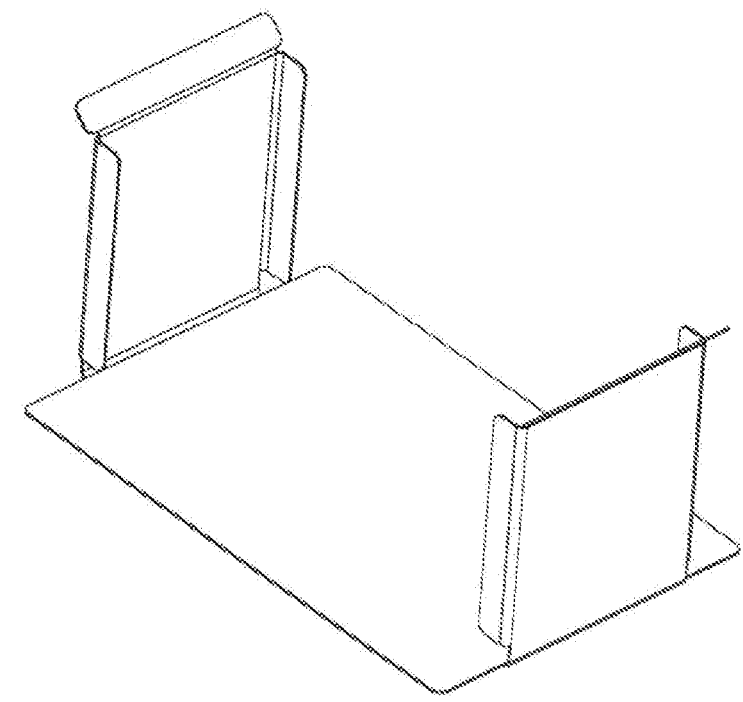
FIG. 8 shows a perspective view of an embodiment of a cradle for releasably storing a plurality of cutting/divider plates ready for use.
Figure 9A:
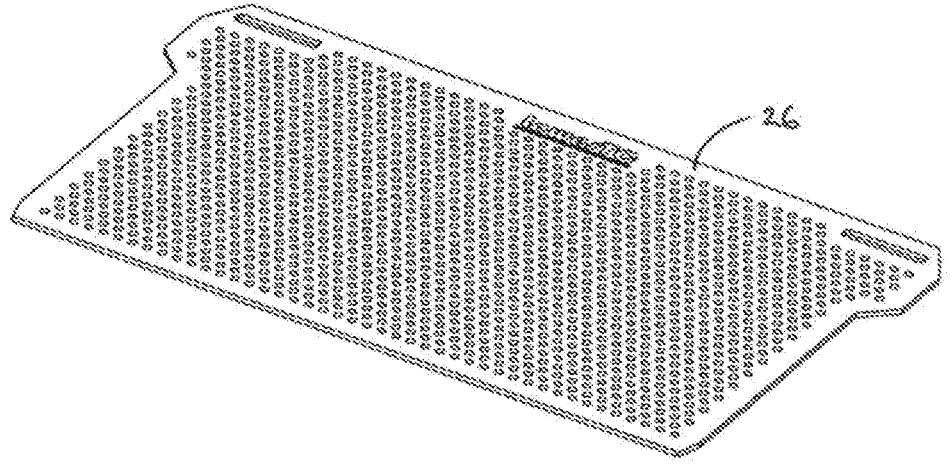
FIGS. 9A and 9B show a perspective view and an enlarged detail view of a leading edge of an embodiment of a cutting/divider plate for dividing a stack of trays into smaller sub-stacks and cutting plants upon insertion between a pair of trays.
Figure 9B:
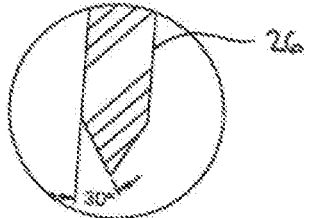

Referring to FIGS. 7 and 9, a cutting mechanism in the form of a dedicated hand-held cutting tool 12 is provided for dividing the stack of trays and manual cutting of the plants growing therein. The cutting tool 12 includes a handle portion 14 at its proximal end and a blade holder 13 at its distal end. The blade holder 13 is adapted to releasably grasp and hold a cutting element in the form of a plate or blade 26 (FIG. 9) such that the blade 26 extends generally away from the handle portion 14 for use. The blade holder 13 can be selectively released to remove the blade 26 for cleaning and storage.

In the illustrated embodiment, the cutting element is in the form of a flat blade 26 (FIG. 9), whereby the blade can fit between a pair of adjacent stacked trays 9 for dividing the stack of trays and cutting each plant growing within the trays 9. In this form, the blade 26 is formed from a relatively thin plate-like material such as, for example, a metal or plastic.

The relatively thin profile of the blade 26 enables it to be inserted between a pair of adjacently stacked trays 9 by a pushing or sliding motion. As is most clearly shown in FIG. 9B, the front edge of the blade 26 is tapered to provide a lead-in, thereby to facilitate insertion of the blade 26 between a pair of stacked trays 9. Advantageously, the lead-in enables the blade 26 to cut each plant from a direction generally transverse or orthogonal to the longitudinal axis of a stem of each plant as the blade 26 is inserted between the respective pair of trays 9. That is, the blade 26 is configured to axially or laterally cut the stem of each plant. In use, the blade can be positioned and manipulated to slide between a pair of trays starting from the front of the stack and progressively moving towards the rear of the stack. In this way, the blade will cut each plant in the first or forwardmost row substantially simultaneously by virtue of the plants being aligned within the respective openings 10, then the second row and so on until the plants within the rearmost row have been cut. Once the blade 26 has been fully inserted and all plants have been cut, the plate-like structure of the blade 26 can be used to support and lift the sub-stack of trays 9 located above the blade 26.

In other forms and rather than employing a blade, the cutting mechanism may include a heat cutting device (not shown) such as for example a laser system or device adapted to pass a laser beam between adjacent trays, or a high pressure nozzle (not shown) adapted to pass a stream of fluid (e.g. water) between adjacent trays or other suitable cutting mechanism such as for example a thin wire element, to effect the cutting operation on the plants in a single pass across the holder. In such forms, the cutting mechanism and the divider/support plate are formed as separate elements or devices.

The cutting operation is preferably performed outside of the bioreactor 2. That is, once the plants have reached the desired growth parameters such as a desired height and/or a set period of time within the bioreactor, in some examples the stack of trays 9 are first removed from the bioreactor 2 before performing the cutting operation.

Figure 10A:
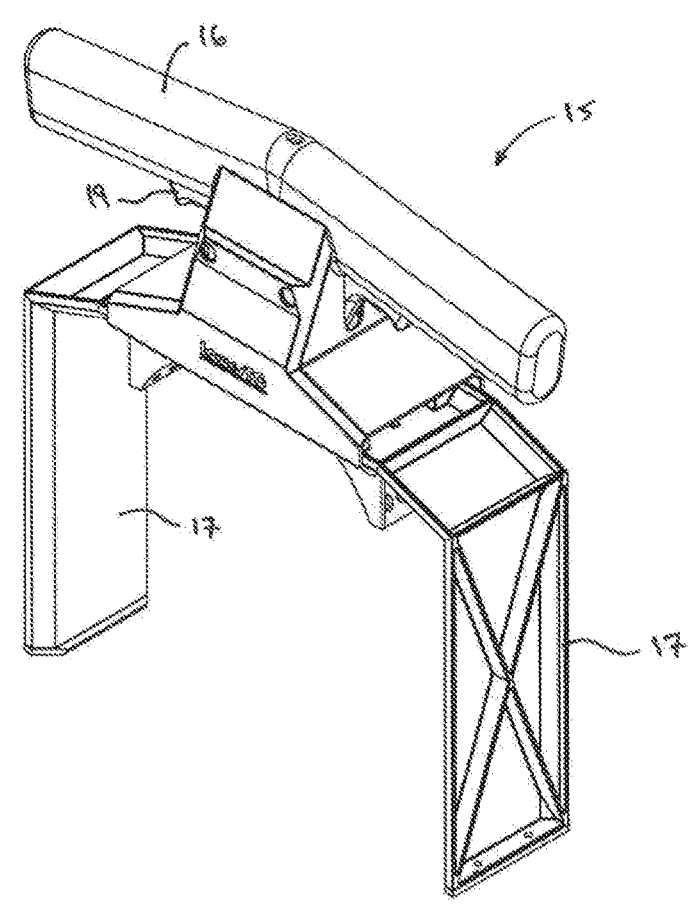
FIGS. 10A and 10B show a perspective view and front view respectively of a carrier for lifting and carrying the stack of trays or a sub-stack of trays.

To assist in lifting the stack of trays 9 together with the plants out of the base portion 3 of the bioreactor 2, a carrier 15 for aseptic handling of a tray or stack of trays 9 is provided. FIG. 10 shows an exemplary embodiment of the carrier 15. The carrier 15 is preferably configured such that it can be used to carry a desired number of plates, from one tray, two or more trays in a sub-stack or the entire stack of trays.

In the illustrated embodiment, the carrier 15 includes a handle 16 and a pair of spaced apart arms 17 extending from the handle 16. The arms 17 are adapted to engage respective side edge portions of the associated tray 9, whereby once the tray is grasped hand manipulation of the carrier 15 via the handle 16 causes a corresponding movement of the grasped tray 9 (and any tray seated above the grasped tray) for positioning as desired (e.g. for aseptically removing the trays 9 from the bioreactor 2). Preferably, the arms 17 extend downwardly from the handle 16, thereby in use to enable the arms to extend into the base portion 3 of the bioreactor 2 from above and thereafter engage the stack of trays 9.

Figure 10B:
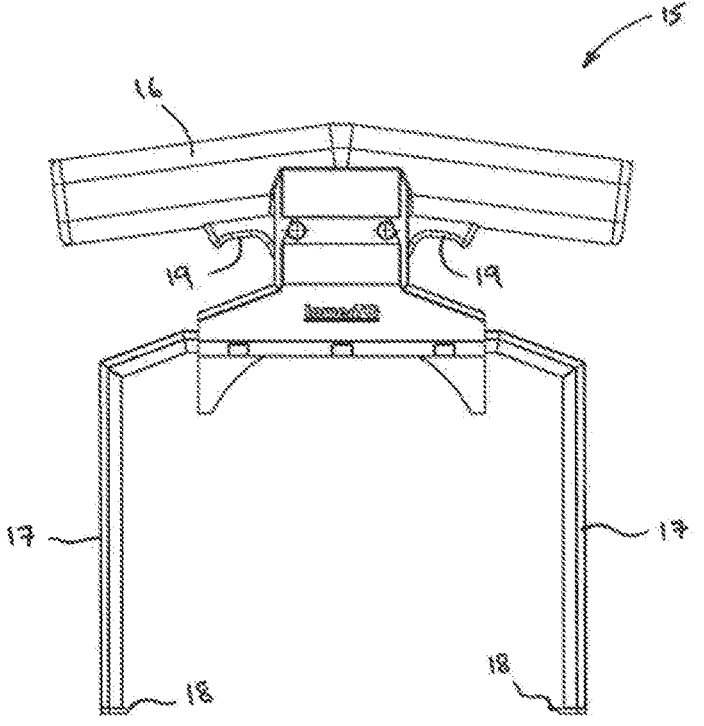

As seen in FIG. 10B, each arm 17 has a tray engaging formation in the form of a transversely extending rail 18 associated with the distal end of the respective arm 17, thereby to facilitate secure engagement or grasping of the respective side edge portions of the tray 9. The side edge portions of each tray 9 may have a receiving formation such as a chamfer, cut-out or recess in which the rail 18 is adapted to be releasably received therein or otherwise engage.

In the illustrated embodiment, the pair of arms 17 are biased towards each other, thereby to facilitate positive engagement with the tray or stack of trays. An operative member in the form of two finger activatable triggers 19 are operatively associated with each arm 17. The triggers 19 are operatively associated with the arms 17 and arranged such that they can be depressed into the handle 16 by finger pressure of a user, whereby operation of the triggers 19 causes the arms 17 (and thus the rails 18) to move away from each other against the action of the biasing mechanism. This helps to widen the gap between the arms 17 and rails 18 so that they can be passed over the stack of trays 9. Subsequently releasing the finger pressure on the triggers 19 and by action of the biasing mechanism (e.g. tensioned coil spring) causes the arms 17 and rails 18 to move inwardly towards each other and thereby engage the respective tray 9.

Figure 6:
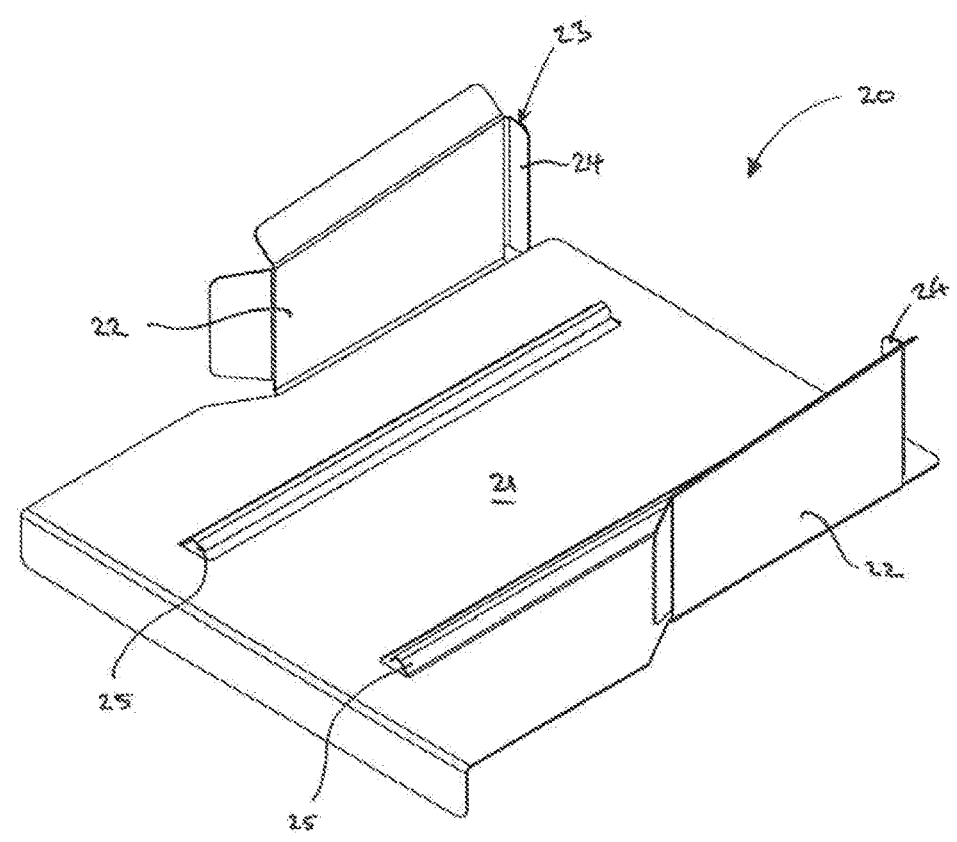
FIG. 6 shows a perspective view of an embodiment of a cradle for supporting a stack of trays during a cutting operation.

Referring to FIG. 6, a cradle 20 is provided for holding a stack of trays in relative alignment upon removal from the bioreactor 2, whereby the passage defined by the aligned openings 10 of the respective trays 9 is maintained in an open position.

In the illustrated embodiment, the cradle 20 includes a floor portion 21 and a pair of side edge portions 22 extending upwardly from the floor portion 21 such that the stack of trays 9 can be received therebetween. The side edge portions 22 are spaced apart by a predetermined distance such that the stack of trays 9 are close fittingly received therebetween, thereby to limit lateral movement of the trays 9 within the cradle 20 and maintain alignment thereof.

In some embodiments, the cradle 20 includes a backstop 23 against which the stack of trays 9 can abut, thereby to limit the extent of rearward movement of the trays relative to the floor portion 21 of the cradle 20. As illustrated, the backstop 23 includes a flange 24 extending transversely from each side edge portion 22, inwardly towards a centre line of the cradle 20.

The front edge of the floor portion 21 of the cradle 20 is folded downwardly so as to form a raising member for raising the front edge of the floor portion relative to its rear edge such that in use the floor portion slopes downwardly from front to back, whereby the stack of trays 9 tends to self-position itself against the backstop by sliding motion.

The floor portion 21 of the cradle 20 includes a friction reducing element in the form of a pair of raised elongate rails 25 for reducing friction between the stack of trays 9 and the floor portion 21. This facilitates ease of relative translational sliding movement of the stack of trays 9 across the floor portion 21 and thus helps to maintain alignment of the stack of trays 9 when transferring the trays 9 to and from the cradle 20.

Referring to FIG. 9, the blade 26 may also function as a divider plate 26 is provided for dividing the stack of trays 9 into smaller sub-stacks after completion of the cutting operation. As before, the divider plate is formed as a perforated thin plate structure such that it can slide between a pair of adjacent vertically stacked trays 9, thereby separating the adjacent pair of trays 9 and forming a platform to assist in lifting a sub-stack of trays off the initial stack. In some forms, the divider plate 26 may also be used to help separate the lowermost tray or trays that are associated with the root system from the trays immediately above which accommodate healthy cuttings.

Referring to FIG. 4, the bioreactor 2 has at least one dedicated nutrient supply port 28 arranged towards a lower region of the container through which a liquid nutrient supply can be selectively charged into and discharged from the bioreactor 2, thereby to promote growth of the plants. In FIG. 4, the bioreactor 2 also has a venting port 27 arranged towards an upper region of the container for intake and exhaust of air to and from the container, thereby to regulate the pressure within the container. That is, the venting port 27 allows air to exhaust from the container as the liquid nutrient supply is charged into the container, thereby to prevent a pressurised atmosphere within the bioreactor. Similarly, as the liquid nutrient supply is discharged from the container, the venting port 27 allows air to pass into the container, thereby to prevent a vacuum pressure occurring within the container, and thus also ensuring that the liquid media freely discharge or drain from the container under gravity to a media container adapted for holding a reservoir of the liquid nutrient supply.

The bioreactor 2 is configured such that when the port 28 is closed the nutrient supply pools on the floor of the base portion 3 such that it is able to come into contact with the root system of the plants.

Figure 11:
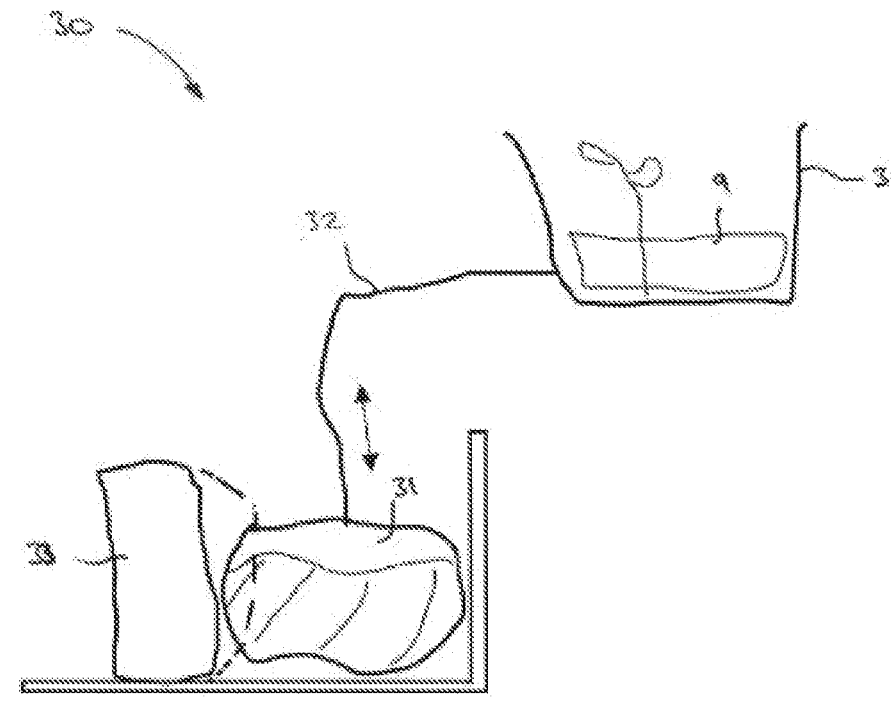
FIG. 11 shows an embodiment of a media delivery system incorporating a flexible nutrient supply container for supplying a liquid nutrient supply to a bioreactor.
Figure 12:
FIG. 12 shows an exemplary arrangement of a media delivery system incorporating a plurality of flexible nutrient supply containers for supplying a liquid nutrient to a plurality of bioreactors.

Referring now to FIGS. 11 and 12, an embodiment of a media delivery system 30 is shown. The system is adapted to be fluidly connectable to the bioreactor 2 via the nutrient supply port 28 for selectively supplying the liquid nutrient supply to an interior of the base portion 3. The media delivery system may be configured as a gravity feed system. In the illustrated embodiment, however, the media delivery system 30 is configured as a pressure feed system.

The media delivery system 30 can be advantageously configured for use in systems for growing various plant types. For example, the system 30 can be used to deliver a nutrient supply 2 under a predetermined dosing regimen to actively promote growth of various types of plants including, but not limited to, arborescent plants and acaulescent plants. The system 30 is particularly advantageous for use in delivering a liquid nutrient supply 2 to plants being grown under plant tissue culture (PTC). The use of a nutrient supply 2 in a flowable or liquid state is advantageous as it can be readily controlled for flow towards and away from the nutrient container as required.

The system 30 will be described therefore, by way of example only, with reference to use in PTC applications. However, the system 30 has potential for use in a broader range of applications and could be readily adapted for use in a variety of other systems, processes and arrangements for growing plants including for example greenhouse and outdoor environments, or liquid dosing requirements for non-plant applications. As described in greater detail below, the system 30 advantageously provides significant flexibility in customising a predetermined or desired dosing regimen for feeding plants with the liquid nutrient supply 2. In particular, the system 1 can be advantageously used to develop a temporary immersion regimen.

The media delivery system 30 advantageously includes a nutrient media container in the form of a flexible bladder or bag 31 for holding a predetermined volume of the nutrient supply or one or more ingredients of the nutrient supply. The flexible bladder 3 is selectively deformable such that, when a compressive force is applied to the bladder 3, at least a portion of the nutrient supply 2 is discharged from the bladder via a port 4. In this way, the liquid nutrient supply 2 can be directed to a bioreactor 5 to promote growth of plants therein.

A supply line 32 is preferably connectable between the bioreactor 2 via the nutrient supply port 28 and the nutrient bag 31 such that the nutrient supply can be charged to and/or discharged from the bioreactor 2, thereby to facilitate running of a predetermined dosing regimen to promote growth of plants within the bioreactor 2.

As is shown in FIG. 11, an activation mechanism 33 in the form of a selectively inflatable bladder is operatively associated with the nutrient bag 31. The activation mechanism 33 is configured for movement between an active position in which the nutrient supply is forced to be charged to the bioreactor 2 (as shown in dashed lines in FIG. 11) and an inactive position in which the nutrient supply is prevented from flowing to the bioreactor 2 (as shown in solid lines in FIG. 11). In some configurations, when the activation mechanism 33 is in the inactive position the nutrient supply drains from the bioreactor 2 via the supply line 32 back to the nutrient bag 31. Such configurations are particularly advantageous for employing temporary immersion dosage regimens, whereby the nutrient supply can be repeatedly charged to and discharged from the bioreactor 2 preferably at predetermined timing intervals.

By employing a flexible nutrient bag 31, the activation mechanism 33 can be readily adapted to compress or squeeze the flexible nutrient bag 31 when in its active position, thereby to force the nutrient supply to flow from the nutrient bag to the bioreactor 2 via the supply line 32. In such embodiments, the activation mechanism disengages or at least partially releases its engagement with the flexible nutrient bag 31 when the activation mechanism returns to its inactive position such that the nutrient supply is free to return to the nutrient container via the supply line 32.

The temporary immersion regimen may be formulated such that a predetermined volume of the nutrient supply is repeatedly charged to the container for a first predetermined discrete interval of time and subsequently discharged from the container for a second predetermined discrete period of time, whereby the charging and discharging of the nutrient supply to and from the container occurs for a predetermined number of cycles and/or over a predetermined duration.

Referring to FIGS. 13A-C, another embodiment of a media delivery system 30 is shown. In this embodiment, the flexible bag 300 has one flow port 400 through which the nutrient supply 200 can flow to or from the flexible bag 300 according to the desired dosing regime. A conduit or supply line in the form of a length of hollow cylindrical tube 600 is provided to direct the flow of the liquid nutrient supply 200 between the flexible bag 300 and the bioreactor 500 in which the plants are to be grown. The conduit 600 is connectable at its first end 700 to the port 400 of the flexible bag 300 and at its second end 800 to a port 900 associated with the bioreactor 500 such that the nutrient supply 200 can be charged to and/or discharged from the bioreactor 500, thereby to facilitate a predetermined dosing regimen to promote growth of plants within the bioreactor 500.

In the illustrated embodiment, the port 900 is formed in a base or floor 1000 of the bioreactor 500. This enables the volume of liquid media supply 200' which is charged to the bioreactor 500 to accumulate or pool across the floor 1000 to a predetermined depth such that it can readily (directly or indirectly) contact the root system of the respective plant or plants in order to provide nutrients thereto and thus promote plant growth.

In the illustrated embodiment, to facilitate control of the flow of liquid nutrient supply 200 to and from the flexible bag 300, the system 100 includes an activation mechanism 1100 operatively associated with the flexible bag 300, whereby operation of the activation mechanism 1100 causes at least a portion of the nutrient supply 200 to flow from the flexible bag 300 to the bioreactor 500 or vice versa.

The activation mechanism 1100 is configured for movement between an active configuration in which the nutrient supply 200 is forced to be charged to the bioreactor 500 (FIG. 13A) and an inactive position in which the nutrient supply 200 cannot flow to the bioreactor 500. To provide control over the operation of the activation mechanism 1100, a selectively operable nutrient supply valve (not shown) is arranged so as to be in fluid communication with the conduit or supply line 600.

The activation mechanism 1100 may include a force applying element or mechanism for applying the compressive force to the flexible bag 300. In the illustrated embodiment, the activation mechanism includes a selectively inflatable element or bladder 1200. The inflatable bladder 1200 is arranged in use such that, upon inflation (i.e. a change in configuration from a deflated or partially/semi-deflated configuration to an inflated or more inflated configuration) it bears against the flexible bag 300 holding the nutrient supply 200, thereby to apply a compressive force to the bag 300 which causes at least a portion of the nutrient supply 200 to flow out of the bag 300, via the conduit 600, to the bioreactor 500.

In the illustrated embodiment, the inflatable bladder 1200 of the activation mechanism 1100 includes at least one receiving formation in the form of a pocket 1300 for releasably receiving at least flexible bag 300. In certain embodiments, the pocket 1300 can take a variety of forms and may, for example, be configured to receive two or more bags 300.

In some embodiments, the inflatable bladder 1200 may include a plurality of pockets 1300 may be formed as an external pocket of the inflatable bladder of the activation mechanism. In some embodiments, one or more pockets may be formed as an internal pocket of the inflatable bladder of the activation mechanism.

Preferably, the or each pocket 1300 includes a window to permit visual inspection of the flexible bag 300 received therein. Similarly, the flexible bag 300 may be formed of a transparent material, thereby to permit visual inspection of the nutrient supply 200 therein.

In use, the inflatable bladder 1200 of the activation mechanism 1100 is connectable to a pressurised fluid (air or liquid) supply, whereby the pressurised fluid supply is selectively operable to inflate and deflate the inflatable bladder as desired. As shown in FIG. 13A, upon inflation of the inflatable bladder 1200, the inflatable bladder 1200 applies a compressive force to the bag 300. This compressive force causes the bag 300 to reduce in size and thereby cause the liquid nutrient supply 200 to be discharged from the bag 300.

Once the desired volume of liquid nutrient supply 200 is transferred from the flexible bag 300 to the bioreactor 500, the conduit valve is closed to hold and retain the discharged nutrient supply 200 in the bioreactor 500 for a predetermined period of time. The compressed air source can then be deactivated, allowing the inflatable bladder 1200 to at least partially deflate such that a compressive force is no longer applied to the flexible bag 300.

After the predetermined time period has elapsed, the valve is opened to allow the nutrient supply 200 within the bioreactor 500 to return to the flexible bag 300. In the illustrated embodiment, the flexible bag 300 is arranged in a position below that of the floor level of the bioreactor 500 such that the when the valve is in its open position, the nutrient supply 200 can freely flow under gravity back to the flexible bag 300. For example, the nutrient supply 2 may be fed to the bioreactor 500 and held therein for a period of 15 minutes per 24-hour period. It will be appreciated that the dosing regime is not limited to this specific example, rather the dosing regimen can be customised to suit the characteristics of the relevant plant type that is being grown and/or the properties of the liquid nutrient supply 200.

Thus, the media delivery system in its various forms provides a number of unique attributes and advantages. In particular, the media delivery system enables the nutrient supply container to be replaced with another to provide a refill and/or to provide a different nutrient to be fed to the plants; for example, it may be beneficial to change the type of nutrient over the course of the growing period to better suit each stage of development of the plants. Advantageously, the nutrient containers can be readily changed without handling or otherwise disturbing the stack of plates and the plants growing therein. This enables plants to be grown for longer periods under the controlled sterile conditions of tissue culture propagation processes. It also reduces the risk of contamination to the plants within the bioreactor, and also enables remedial actions to be taken to remove certain identified sources of contamination without the need to handle or otherwise disturb the plants and/or stack of plates. Furthermore, in the present system, any contamination that does occur can be controlled by adding a sterilant to the growth media without having to handle or move the plants.

A nutrient controller (not shown) may be operatively associated with the media delivery system 30 to facilitate autonomous or semi-autonomous control of the dosing regimen. In other forms, the media delivery system may be operated manually by a user.

Figures 15A, 15B, 15C:
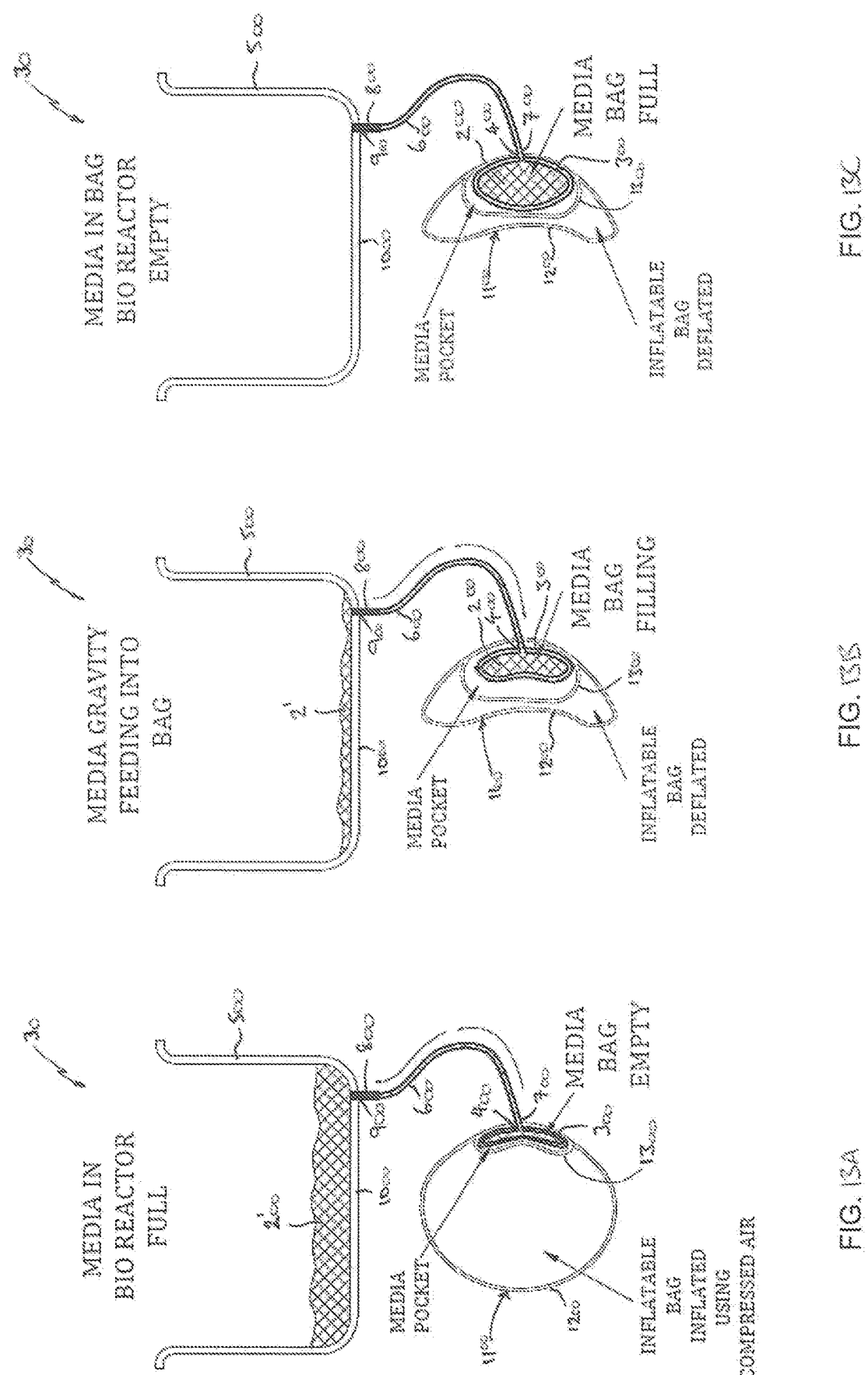
FIG. 15 shows a schematic diagram of an embodiment of a tray of a plant propagation according to the present disclosure, with a plurality of plants growing in respective plant receiving openings.
Figure 14:
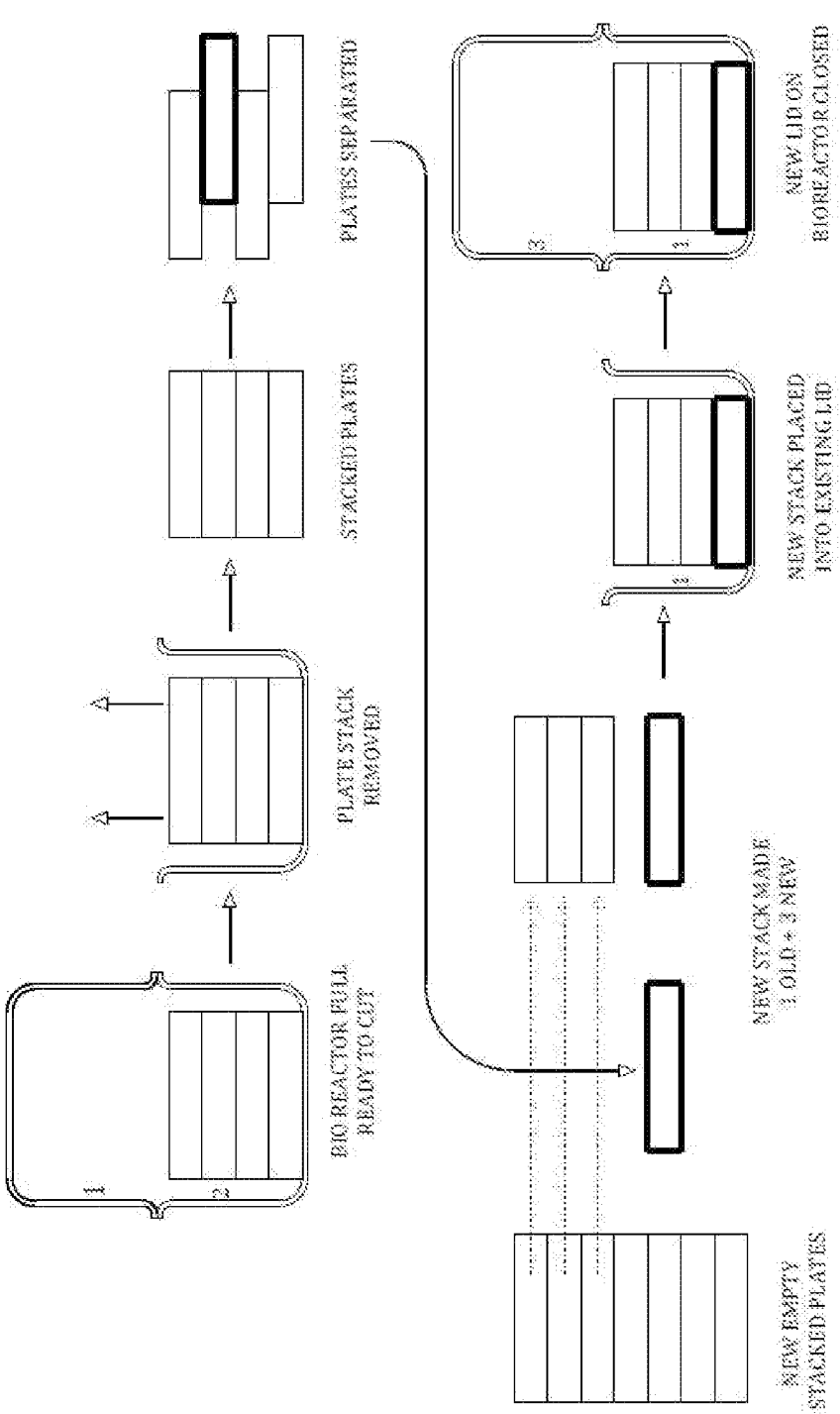
FIG. 14 is a process diagram showing an overview of process of growing plants through a stack of trays, cutting the plants and dividing the stack, and repeating the process with each tray holding cut plants.

Referring to FIGS. 15 to 17 another embodiment of a plant propagation system 50 is shown. This system 50 is particularly advantageous for use in processes for growing acaulescent plants, particularly by way of plant tissue culture (PTC). As used herein, the term acaulescent plants is understood to include plants which typically have little or no stem above ground or soil level. Acaulescent plants are sometimes referred to as tufted or rosette type plants.

This plant propagation system includes a tray 51 having a plurality of plant receiving cavities or openings 52 for receiving a growing plant 53. In the illustrated exemplary embodiment, the tray is shown with six plant receiving openings 52. Preferably, each plant receiving opening 52 receives a single plant 53.

It will be appreciated from the following description of the present invention that the tray 52 is not limited to having merely six plant receiving openings 52. Rather in practical commercial applications of the present plant propagation system it will be appreciated that the efficiency of the system increases with the number of plants that can be grown in a single tray 51 and thus the number of plant receiving openings 52 in the tray 51. The use of six plant receiving openings 52 in the illustrated embodiment is merely to demonstrate the concept of the present plant propagation system in a clear manner.

As is described in further detail below, the tray 51 is typically placed in a bioreactor (not shown) so as to rest on a floor thereof. It will be appreciated therefore that, by provision of the array of plant receiving openings 52, the tray 51 advantageously provides a structure for growing a plurality of plants 53 in an ordered manner with dedicated locations for each individual plant 53 within the bioreactor.

In the illustrated embodiment, the tray 51 is generally rectangular in shape and of uniform thickness or height. In some forms, the tray 51 is sized to be close-fittingly received within the bioreactor thereby to assist in locating and positioning the tray 51 within the bioreactor, either in a lengthwise direction, from side-to-side or both. In some forms, the tray 51 may include one or more locating formations extending from or otherwise associated with a peripheral edge of the tray 51 in order to facilitate locating and positioning the tray 51 within the bioreactor.

The size and shape of the plant receiving openings 52 is selected preferably with reference to the plant type which is intended to be grown therein. In particular, the size and shape of the plant receiving openings 52 is selected so as to accord with the natural growing tendencies of the respective plant 53. For example, some plant types have a natural tendency to grow in a generally round or ball shape such that a tray 51 having circular shaped plant receiving openings 52 is preferred. Other plant types have a natural tendency to grow along a single axis such that a tray 51 having rectangular shaped plant receiving openings 52 is preferred. It will be appreciated that the shape of the openings 52 is not limited to the exemplary forms described above. Rather in various embodiments, each opening 52 could be square, triangular, hexagonal or other suitable polygonal shape.

In the illustrated embodiment, each plant receiving opening 52 is an open-topped opening or cavity. Each open-topped opening or cavity 52 preferably has a perforated floor 4 with one or more openings (not shown), thereby to facilitate feeding of a liquid nutrient supply to a root system of the plant 53 growing within the respective opening 52.

In addition, the floor 54 of each plant receiving opening 52 can also assist when it is desired to lift and remove the tray 51 from the bioreactor for further processing; for example, when the plants 52 reach a predetermined desired stage of growth development. The floor 54 may bear against the lowerside of the respective plant 53, thereby to stabilise or otherwise limit movement of the plant during one or more subsequent further processing steps (e.g. a cutting process).

In this regard, the plant propagation system further includes a cutting element (not shown) which is adapted to make at least one cut in each individual plant 53 growing in the tray 51, thereby to divide the plant 53 into two or more smaller sub-plant portions 55.

The cutting process takes place once the plants 53 reach a predetermined stage of development. The stage of development may be determined according to a period of time over which the plant 53 is grown in the tray and/or the size of the plant 53 or other relevant characteristic of the plant.

Preferably, the cutting element is configured to cut or divide each plant 53 evenly, whereby each cut plant portion 55 is of substantially the same size. In the illustrated embodiment as shown in FIG. 2, the cutting element is configured making a cutting action along two orthogonally arranged cutting lines. The cutting lines intersect at the central point of the respective opening 52 in the tray 51. In this embodiment, the cutting element cuts or divides each plant 3 into four smaller plant portions 5 of substantially equal size or, in other words, the cutting element is used to quarter each plant 3.

The manner in which the cutting element cuts or divides each plant may be determined in relation to the shape or configuration of the cutting element itself. In some forms, the cutting element is adapted to divide each plant into the predetermined smaller plant portions in a single cutting action. In other forms, the cutting element is adapted to divide each plant into the predetermined smaller plant portions with two or more cutting actions, strokes or passes.

For example, where the cutting element is in the form of a blade having a single cutting edge, the cutting element may be employed to cut or divide the plant in half through a first cutting action such as a downward or descending movement of the blade towards the tray and into a respective opening or cavity 52. After the first cutting action, in this example, the blade may be turned relative to the tray (and/or the tray may be turned relative to the blade) by a predetermined extent or angle (e.g. 90 degrees) such that the cutting element can make a second cutting action to further divide the plant (e.g. cut each of the half plant portions formed by the first cutting action into quarter plant portions).

In other forms, the cutting element may include a blade which is configured to quarter each plant with a single cutting action or pass. For example, the blade may be generally t- or plus-sign ("+") shaped, thereby to cut or divide the plant into four plant portions 55.

The shape and configuration of the cutting element can be adapted to suit a particular application or plant type and/or to cut or divide the plant in a particular manner. In some forms, the cutting element may be straight-edged, bevelled, chamfered, serrated, saw-toothed or the like, thereby to enhance its cutting ability in terms of strength of cut (e.g. cutting thicker and/or tougher plants) and/or coarse of cut/accuracy (e.g. fine to coarse cutting).

It will be appreciated that the cutting element is not limited to having a cutting blade as shaped according to the above non-limiting exemplary forms which have been provided only by way of example.

The cutting element may include a handle portion extending away from the blade, thereby to facilitate hand manipulation of the cutting element and manual cutting of plants 53 growing within the tray 51. In some applications, the cutting element is adapted to be attached to a selectively operable actuator, thereby to facilitate autonomous and semi-autonomous cutting processes.

In such embodiments, the actuator may be adapted to facilitate movement of the cutting element towards and away from the tray 51, thereby to cause the cutting action for cutting or dividing the respective plant or plants growing within the tray. For example, the actuator may be a linear actuator configured to cause corresponding linear movements (e.g. upward and downward movement) of the cutting element. In other forms, the actuator may include a first actuator for effecting linear positional movement of the cutting element and a second actuator for effecting rotary positional movement of the cutting element, thereby to facilitate positioning and alignment of the cutting element relative to the tray and thus the respective plant growing therein. In yet other forms, the cutting element may form the end effector of a robotic arm, whereby the robotic arm is configured to control movement of the cutting element and thus the associated cutting action including, for example, cutting speed, frequency, timing, etc.

A single cutting element may be used to cut each plant 53 growing in the tray 51. For example, the cutting element may be employed to perform a cutting action in each opening 52 of the tray 51 according to a predetermined routine (e.g. successively across the first row, then the second row and so on). Alternatively, the cutting element is used to perform the cutting action on a plant by reference to a predetermined growing period of each plant or development stage (e.g. size or shape) of each plant.

The cutting element may be adapted to cut a plurality of plants 53 during a single cutting operation. For example, the cutting element may include a plurality of blades arranged in relative spaced apart relation, wherein the spacing between blades corresponds to the spacing between the openings of the tray in which simultaneous cuts is desired. With such cutting elements, the blades may be spaced apart such that each plant in a first row of the tray is cut simultaneously. In some exemplary forms, the cutting element may be adapted to cut each plant growing within a plant 53 receiving formation of the tray 51 simultaneously.

The plant propagation system preferably includes a cover (not shown) which is releasably mountable to or adjacent an upper surface of the tray 51. The cover may be mounted to the tray 51 to constrain or limit the height to which each plant 53 can grow. The cover may be adapted to cut or trim the plants upon removal of the cover from the tray such that each trimmed plant has substantially the same height. For example, the cover may be slidably mounted to the tray, whereby upon sliding action to remove the cover from the tray, the tray shears the plants to trim the shoots projecting above the height of the cover. In other forms, a dedicated plant trimming device may be provided for trimming the plants to a desired height.

The plant propagation system preferably includes a plurality of trays 51 wherein a first tray 51 (FIG. 1) is used to grow a first batch of plants 53, and a second tray 51' (FIG. 3) is used to grow a second batch of plants 53 from plant portions 55 cut from the first batch of plants 53. Additional trays can be used to grow further batches from subsequent cut plant portions.

The extraction of the cut plant portions 55 can be performed as a manual operation, optionally performed by hand or with the aid of a dedicated plant grasping mechanism. Where a plant grasping mechanism is used, the grasping mechanism may be attached to an actuator such as for example, a linear actuator, a rotary actuator or a robotic arm, to facilitate autonomous or semi-autonomous removal of the cut plant portions from the tray and subsequent transfer to another tray to recommence the growing process.

It can be advantageous to retain the cutting element in place at the end of the cutting action within the respective plant receiving opening, whilst the cut plant portions are removed from the cavity 52/tray 51. By retaining the cutting element in this position during removal of the cut plant portion, there is a reduced risk of inadvertently removing another of the cut plant portions during the extraction process.

It will be appreciated that plant propagation system can advantageously be used to grow batches of plants in a controlled and repeatable manner. It provides a means by which plants can be cut into uniform sub-plant portions. The ability to easily cut multiple plants into sub-potions of uniform size at relative high speed, particularly via an autonomous or semi-autonomous process, greatly increases the efficiency of the overall plant propagation process based on plant tissue culture (PTC). This primarily arises by virtue of the ability to decrease the cutting time per plant, as well as the time to transfer and replant (e.g. in another tray) the cut-plant portions to repeat the growing cycle. The uniform nature of the cut sub-portion also enhances the likely success or survival rate of growing these sub-plant portions to a desired stage of development. This process can be repeated to continue the growing cycle.

Thus, the present disclosure in its various forms provides a number of unique attributes and advantages, including the ability to hold a plurality of plant tissue culture in clearly defined regularly spaced locations within a bioreactor, providing significant improvements in the efficiency in which cloned cuttings can be produced. The ability of the system to allow multiple cuttings to be made during a single pass of a cutting operation leads to benefits in terms of a greater of number of cuttings that can be produced over a set period of time. The ability to significantly produce more cuttings over a given period advantageously enables operational costs including labour costs to be dramatically reduced, thereby reducing the cost per cutting produced under plant tissue culture propagation.

In addition, as noted above, the system enables the nutrient supply container to be replaced with another to provide a refill and/or to provide a different nutrient to be fed to the plants; for example it may be beneficial to change the type of nutrient over the course of the growing period to better suit each stage of development of the plants.

The system is also highly adaptable in terms of its ability to be configured for use with upstream and downstream automation equipment associated with incubation and harvesting processes, further enhancing the overall operational efficiency and reducing the costs associated with production of plant tissue culture. In this regard it is a further advantage of preferred embodiments of the disclosure to provide a system that can deliver PTC in a form compatible with existing greenhouse automation equipment and reduce the labour requirement. More specifically, embodiments of the present disclosure advantageously enable a tray containing plants that have reached a predetermined stage of development in the bioreactor to be transferred to a greenhouse or outdoor environment directly from the bioreactor in the same tray. That is, the plants can stay within the original tray rather than being transferred to a new tray, reducing the handling time and thus associated labour costs. This particular advantage arises from the use of a liquid media or nutrient supply in the initial stage of growth within the bioreactor. Once the tray has been transferred to the greenhouse or outdoor environment, the plants can then grow to the stage of a fully functioning plant and manipulated with existing equipment including automation equipment. Here it can be advantageous to provide each tray with connectors that facilitate connecting multiple trays in a side-by-side and/or end-to-end arrangement to effectively produce a larger combined tray that is sized such that it can be carried from a sterile environment (e.g. laboratory) to a non-sterile environment (e.g. a greenhouse or outdoor environment) via existing (automation) equipment and other related handling equipment.

It will be appreciated therefore that the system is inherently capable of making plant tissue culture propagation far more cost effective than existing techniques and in some instances comparable to the costs associated with seeding techniques.

In these and other respects, the systems and approaches described herein represent a practical and commercially significant improvement over existing systems. Although the present disclosure has been described with reference to specific examples, it will be appreciated by those skilled in the art that the systems and approaches described herein may be embodied in many other forms.

The invention claimed is:

1. A plant propagation system, including:
a container; and
a holder for holding at least two plants in relative spaced apart relation;
wherein the holder includes two or more trays stacked to form a stack of trays, wherein each tray has the same shape and configuration, and wherein each tray has a plurality of through openings, respective through openings of the trays in the stack of trays being aligned to form through passages through which the plants can grow; and
wherein,
(a) the plurality of through openings in each tray are all the same shape,
(b) the plurality of through openings in each tray are all the same size, and/or
(c) each tray has the same profile and pattern of openings; and
wherein the stack of trays is releasably receivable in the container and formed such that, when the stack of trays is removed from the container, a cutting mechanism can effect a lateral cutting operation on the plants between a respective pair of adjacent trays in the stack of trays.

2. A plant propagation system according to claim 1, wherein each of the plurality of openings is configured to receive at least a portion of one of the at least two plants.

3. A plant propagation system according to claim 2, wherein the plurality of openings in each tray are arranged in a regular array.

4. A plant propagation system according to claim 2, wherein the plurality of openings in each tray are arranged in an irregular array.

5. A plant propagation system according to claim 1, further comprising the cutting mechanism, wherein the cutting mechanism includes a hand-held cutting tool for manual cutting of the at least two plants.

6. A plant propagation system according to claim 1, further comprising the cutting mechanism, wherein the cutting mechanism includes a cutting element adapted to be slidably received between the respective pair of adjacent trays to cause the lateral cutting operation on the at least two plants.

7. A plant propagation system according to claim 1, wherein the container has a base portion and an open top for releasably receiving the stack of trays therein, and a lid portion releasably attachable about the open top of the base, thereby to close the container.

8. A plant propagation system according to claim 7, including a media delivery system for selectively supplying a nutrient supply to the container.

9. A plant propagation system according to claim 8, wherein the media delivery system is a pressure feed system.

10. A plant propagation system according to claim 8, wherein the media delivery system includes a nutrient container for holding a predetermined volume of the nutrient supply; and
an activation mechanism operatively associated with the nutrient container, whereby operation of the activation mechanism causes at least a portion of the nutrient supply to flow from or to the nutrient container.

11. A plant propagation system according to claim 10, wherein the nutrient container is flexible, wherein the activation mechanism can selectively deform the nutrient container to cause the nutrient supply to flow from the nutrient container to the container via a supply line.

12. A plant propagation system according to claim 1, further including a carrier for aseptic handling of the stack of trays.

13. A plant propagation system, including:
a container; and
a holder for holding at least two plants in relative spaced apart relation;
wherein the holder includes two or more trays stacked to form a stack of trays, wherein each tray has the same shape and configuration, and wherein each tray has a plurality of through openings, respective through openings of the trays in the stack of trays being aligned to form through passages through which the plants can grow;
wherein the stack of trays is releasably receivable in the container and formed such that, when the stack of trays is removed from the container, a cutting mechanism can effect a lateral cutting operation on the plants between a respective pair of adjacent trays in the stack of trays;
wherein each of the plurality of openings is configured to receive at least a portion of one of the at least two plants; and
wherein the plurality of openings in each tray are arranged in an irregular array.

14. A plant propagation system, including:
a container;
a holder for holding at least two plants in relative spaced apart relation; and
a cutting mechanism;
wherein the holder includes two or more trays stacked to form a stack of trays, wherein each tray has the same shape and configuration, and wherein each tray has a plurality of through openings, respective through openings of the trays in the stack of trays being aligned to form through passages through which the plants can grow;
wherein the stack of trays is releasably receivable in the container and formed such that, when the stack of trays is removed from the container, a cutting mechanism can effect a lateral cutting operation on the plants between a respective pair of adjacent trays in the stack of trays; and
wherein the cutting mechanism includes at least one of: a hand-held cutting tool for manual cutting of the at least two plants or a cutting element adapted to be slidably

US 12,672,620 B2

37 / 38 received between the respective pair of adjacent trays to cause the lateral cutting operation on the at least two plants.

* * * * *